US011800970B2

(12) United States Patent
Govari et al.

(10) Patent No.: US 11,800,970 B2
(45) Date of Patent: Oct. 31, 2023

(54) COMPUTERIZED TOMOGRAPHY (CT) IMAGE CORRECTION USING POSITION AND DIRECTION (P AND D) TRACKING ASSISTED OPTICAL VISUALIZATION

(71) Applicants: Biosense Webster (Israel) Ltd., Yokneam (IL); Acclarent, Inc., Irvine, CA (US)

(72) Inventors: Assaf Govari, Haifa (IL); Vadim Gliner, Haifa (IL); Babak Ebrahimi, Irvine, CA (US); Ehsan Shameli, Irvine, CA (US); Fatemeh Akbarian, Rancho Palos Verdes, CA (US); Jetmir Palushi, Irvine, CA (US); Yehuda Algawi, Binyamina (IL)

(73) Assignees: Biosense Webster (Israel) Ltd., Yokneam (IL); Acclarent, Inc., Irvine, CA (US)

( * ) Notice: Subject to any disclaimer, the term of this patent is extended or adjusted under 35 U.S.C. 154(b) by 0 days.

(21) Appl. No.: 17/881,755

(22) Filed: Aug. 5, 2022

(65) Prior Publication Data
US 2023/0023881 A1    Jan. 26, 2023

Related U.S. Application Data

(63) Continuation of application No. 16/588,955, filed on Sep. 30, 2019, now Pat. No. 11,457,981.
(Continued)

(51) Int. Cl.
*A61B 5/00*    (2006.01)
*A61B 1/00*    (2006.01)
(Continued)

(52) U.S. Cl.
CPC ...... *A61B 1/000094* (2022.02); *A61B 1/0004* (2022.02); *A61B 1/0005* (2013.01);
(Continued)

(58) Field of Classification Search
CPC ............ A61B 1/00097; A61B 1/00194; A61B 1/00096; A61B 5/052; A61B 5/066; A61B 2034/2051; A61B 2034/2065
See application file for complete search history.

(56) References Cited

U.S. PATENT DOCUMENTS

| | | | |
|---|---|---|---|
| 2008/0212838 A1* | 9/2008 | Frigerio | G06T 7/223 382/107 |
| 2013/0211588 A1* | 8/2013 | Diolaiti | B25J 9/1689 700/249 |

(Continued)

*Primary Examiner* — Joel F Brutus
(74) *Attorney, Agent, or Firm* — Frost Brown Todd LLP

(57) ABSTRACT

A system (11) includes a medical probe (36) for insertion into a cavity of an organ, which includes a position and direction sensor (60) and a camera (45), both operating in a sensor coordinate system (62). The system further includes a processor (44) configured to: receive, from an imaging system (21) operating in an image coordinate system (28), a three-dimensional image of the cavity including open space and tissue; receive, from the medical probe, signals indicating positions and respective directions of the medical probe inside the cavity; receive, from the camera, respective visualized locations inside the cavity; register the image coordinate system with the sensor coordinate system so as to identify one or more voxels in the image at the visualized locations, and when the identified voxels have density values in the received image that do not correspond to the open space, to update the density values of the identified voxels to correspond to the open space.

20 Claims, 15 Drawing Sheets

Related U.S. Application Data

(60) Provisional application No. 62/741,403, filed on Oct. 4, 2018.

(51) Int. Cl.
    *A61B 34/20*     (2016.01)
    *A61B 5/06*     (2006.01)
    *A61B 6/03*     (2006.01)
    *G06T 15/08*     (2011.01)
    *G06T 7/593*     (2017.01)

(52) U.S. Cl.
    CPC ...... *A61B 1/00096* (2013.01); *A61B 1/00097* (2022.02); *A61B 1/00193* (2013.01); *A61B 1/00194* (2022.02); *A61B 5/062* (2013.01); *A61B 5/066* (2013.01); *A61B 6/032* (2013.01); *A61B 34/20* (2016.02); *G06T 7/593* (2017.01); *G06T 15/08* (2013.01); *A61B 2034/2051* (2016.02); *A61B 2034/2065* (2016.02); *G06T 2207/10028* (2013.01); *G06T 2207/10081* (2013.01); *G06T 2210/41* (2013.01)

(56) References Cited

U.S. PATENT DOCUMENTS

| | | | |
|---|---|---|---|
| 2015/0031951 A1* | 1/2015 | Furlong | A61B 1/00133 600/106 |
| 2016/0073855 A1* | 3/2016 | Farr | A61B 1/0615 600/109 |
| 2017/0084036 A1* | 3/2017 | Pheiffer | G06T 7/35 |

* cited by examiner

COMPUTERIZED TOMOGRAPHY (CT) IMAGE CORRECTION USING POSITION AND DIRECTION (P AND D) TRACKING ASSISTED OPTICAL VISUALIZATION

CROSS-REFERENCE TO RELATED APPLICATIONS

This application is a continuation of U.S. patent application Ser. No. 16/588,955, entitled "Computerized Tomography (CT) Image Correction Using Position and Direction (P&D) Tracking Assisted Optical Visualization," filed Sep. 30, 2019, and issued as U.S. Pat. No. 11,457,981 on Oct. 4, 2020, which claims the benefit of U.S. Provisional Patent Application 62/741,403, filed Oct. 4, 2018, whose disclosure is incorporated herein by reference.

FIELD OF THE INVENTION

The present invention relates generally to medical imaging, and particularly to updating an outdated medical image while performing an invasive medical procedure.

BACKGROUND OF THE INVENTION

During a medical procedure, a real-time representation of an anatomy probed by a medical device, such as by a probe tracked by a position tracking system, can be superimposed on pre-acquired medical images so as to improve the anatomy representation. For example, U.S. Patent Application Publication 2018/0146883, issued as U.S. Pat. No. 10,299,699 on May 28, 2019, describes methods, apparatuses and computer program products that include receiving, from an imaging system operating in an image coordinate system, a three-dimensional image of a body cavity including open space and body tissue, and receiving, from a medical probe having a location sensor and inserted into the body cavity, a signal indicating a location of a distal tip of the medical probe in a sensor coordinate system. The image coordinate system is registered with the sensor coordinate system so as to identify one or more voxels in the three-dimensional image at the indicated location, and when the identified voxels have density values in the received three-dimensional image that do not correspond to the open space, the density values of the identified voxels are updated to correspond to the open space.

As another example, U.S. Patent Application Publication 2014/0147027, issued as U.S. Pat. No. 10,345,844 on Jul. 9, 2019, describes an imaging correction system that includes a tracked ultrasonic imaging probe configured to generate imaging volumes of a region of interest from different positions. An image compensation module is configured to process image signals from an ultrasound imaging device associated with the probe and to compare one or more ultrasound image volumes with a reference, such as CT images, to determine, using an image compensation module, aberrations in ultrasonic imaging and generate a corrected ultrasound image for display based on compensating for the aberrations.

Image-guided surgery (IGS), such as described above, is a technique where a computer is used to obtain a real-time correlation of the location of an instrument that has been inserted into a patient's body to a set of preoperatively obtained images (e.g., a CT or MRI scan, 3D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif.

In some IGS procedures, a digital tomographic scan (e.g., CT or MRI, 3D map, etc.) of the operative field is obtained prior to surgery. A specially programmed computer is then used to convert the digital tomographic scan data into a digital map. During surgery, special instruments having position sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While IGS navigation systems provide useful views and information during a surgical procedure, a surgeon may also desire real-time photographs and video of an anatomical structure being operated on. In such cases, an endoscope may be deployed to the surgical site with the aid of IGS navigation in order to capture images of the anatomical structure; and may also be paired with or otherwise deployed with other surgical instruments, such as cutting instruments, ablation instruments, dilation catheters, etc. Photographic images and video captured in this manner may be more useful than IGS navigation images, which may only provide generalized and simulated images. Alternatively, photographic images and video captured in this manner may provide a useful supplement to IGS navigation images.

Images captured by a conventional endoscope may also be somewhat limited as compared to direct visual observation by a surgeon, as images captured with a conventional endoscope may be limited to two-dimensional (2D) representations of an anatomical structure. Operation such as cutting, ablating, dilating, etc. may be performed using a combination of 2D endoscopy and IGS navigation, neither of which can provide the sense of depth perception available with true three-dimensional (3D) observation. Manipulating and operating surgical tools without the benefit of 3D observation can increase the time spent positioning tools; and can increase the possibility of error. While some 3D endoscopic cameras exist, they have a high complexity and cost; and may have rigid and inflexible portions that make them difficult or impossible to use for some procedures. Implementations having both flexibility and 3D features may require expensive and fragile fiber optic components to transfer captured images from a distal camera to a proximal viewer. As a result, conventional options for 3D endoscopy may be expensive, limited in available features, and unsuitable for high volume use and disposability.

While several systems and methods have been made and used in surgical procedures, it is believed that no one prior to the inventors has made or used the invention described in the appended claims.

SUMMARY OF THE INVENTION

An embodiment of the present invention provides a system including a medical probe, a position and direction sensor, a camera, and a processor. The medical probe is configured to be inserted into a cavity of an organ of a patient. The position and direction sensor is in the medical probe and is operating in a sensor coordinate system. The camera is in a distal edge of the medical probe and is operating in a sensor coordinate system. The processor configured to: (a) receive, from an imaging system operating in an image coordinate system, a three-dimensional image of the cavity including open space and organ tissue, (b) receive, from the medical probe, signals indicating positions and respective directions of the distal edge of the medical probe inside the cavity, (c) receive, from the camera of the probe, respective visualized locations inside the cavity, (d) register the image coordinate system with the sensor coordinate system so as to identify one or more voxels in the three-dimensional image at the visualized locations, and (e) when the identified voxels have density values in the received three-dimensional image that do not correspond to the open space, to update the density values of the identified voxels to correspond to the open space.

In some embodiments, the imaging system includes a computed tomography scanner.

In some embodiments, the position and direction sensor includes a magnetic field sensor.

In an embodiment, the processor is configured to form a correspondence between the density values visual effects, wherein a given visual effect corresponds to a given density value indicating the open space. In another embodiment, the visual effects are selected from a group consisting of colors, shadings and patterns.

In some embodiments, the processor is configured to present the three-dimensional image on a display using the visual effects. In other embodiments, the given visual effect includes a first given visual effect, and, prior to updating the density values, the processor is configured to present the three-dimensional image by presenting, using a second given visual effect different from the first given visual effect, the one or more identified voxels.

In an embodiment, upon updating the density values, the processor is configured to present the three-dimensional image by presenting, using the first given visual effect, the one or more identified voxels. In another embodiment, the processor is configured to, using a multi-view triangulation model, extract from the visual signals a distance of a location from the camera.

There is additionally provided, in accordance with an embodiment of the present invention, a method, including receiving, from an imaging system operating in an image coordinate system, a three-dimensional image of a cavity of an organ of a patient including open space and organ tissue. Signals indicating positions and respective directions of a distal edge of the medical probe inside the cavity, and respective visualized locations inside the cavity, are received from a medical probe having a position and direction sensor and a camera, wherein the probe operates in a sensor coordinate system and inserted into the cavity. The image coordinate system is registered with the sensor coordinate system so as to identify one or more voxels in the three-dimensional image at the visualized locations. When the identified voxels have density values in the received three-dimensional image that do not correspond to the open space, the density values of the identified voxels are updated to correspond to the open space.

There is further provided, in accordance with an embodiment of the present invention, computer software product, operated in conjunction with a probe that is configured for insertion into a cavity of an organ of a patient and includes a position and direction sensor operating in a sensor coordinate system and a camera in a distal edge of the medical probe operating in a sensor coordinate system, and the product including a non-transitory computer-readable medium, in which program instructions are stored, which instructions, when read by a computer, cause the computer to (a) receive, from an imaging system operating in an image coordinate system, a three-dimensional image of the cavity including open space and organ tissue, (b) receive, from the medical probe, signals indicating positions and respective directions of the distal edge of the medical probe inside the cavity, (c) receive respective visualized locations the wall of the cavity, (d) register the image coordinate system with the sensor coordinate system so as to identify one or more voxels in the three-dimensional image at the visualized locations, and (e) when the identified voxels have density values in the received three-dimensional image that do not correspond to the open space, to update the density values of the identified voxels to correspond to the open space.

There is furthermore provided, in accordance with an embodiment of the present invention, a three-dimensional (3D) imaging system including an endoscope and a processor. The endoscope includes: (i) a shaft having a distal tip, the shaft adapted to be inserted into a patient and positioned at a surgical site of the patient, (ii) a position sensor proximate to the distal tip and configured to produce a set of position signals based on the location of the endoscope during use, and (iii) an imaging module positioned at the distal tip and operable to capture a set of image data of the surgical site, wherein the set of image data includes one or more two-dimensional (2D) images. The processor is communicatively coupled with the endoscope and configured to: (i) receive the set of image data and the set of position signals from the endoscope, (ii) determine a set of perspective data based on the set of position signals, wherein the set of perspective data indicates the location of the endoscope during capture of each of the one or more 2D images, (iii) perform an image depth analysis to determine a set of 3D characteristics for each of the one or more 2D images, wherein the set of 3D characteristics includes a depth of pixels, (iv) create a set of 3D image data based on the one or more 2D images and the set of 3D characteristics, and (v) associate the set of perspective data with the set of 3D image data, wherein the image depth analysis includes a technique selected from the group consisting of: (i) a wavefront sampling technique performed on a single image of the one or more 2D images, and (ii) a passive stereo vision technique performed on a set of two images of the one or more 2D images, wherein each of the set of two images are associated with the same perspective data.

In some embodiments, the imaging module includes: (i) a single lens, (ii) an aperture plate positioned between a first side of the single lens and the surgical site, the aperture plate including one or more apertures that are offset from the optical axis of the single lens, and (iii) an image pane positioned at a second side of the single lens to receive reflected light from the surgical site via the one or more apertures and the single lens, wherein the image pane is configured to produce the set of image data based on the reflected light.

In some embodiments, (i) the one or more apertures include at least two apertures positioned on the aperture plate and offset from the optical axis of the single lens, and (ii) the aperture plate has a fixed position and orientation relative to the lens.

In an embodiment, (i) the one or more apertures include a single aperture positioned on the aperture plate offset from the optical axis of the single lens, (ii) the aperture plate is operable to rotate around its circular axis relative to the lens during image capture.

In another embodiment, the processor is configured to, when performing the image depth analysis: (i) identify, within the set of image data, two or more unfocused images of the surgical site, (ii) determine a spatial relationship between the two or more unfocused images of the surgical site, and (iii) determine the depth of pixels of the set of image data based on the spatial relationship between the two or more unfocused images.

In some embodiments, the imaging module includes two or more cameras, and wherein each of the two or more cameras is: (i) statically positioned relative to every other camera of the two or more cameras, (ii) oriented to have a parallel optical axis with every other camera of the two or more cameras.

In some embodiments, the processor is further configured to, when performing the image depth analysis, (i) identify a point in a first image of the set of image data, wherein the point includes a portion of the surgical site that is present within both the first image captured by a first camera of the two or more cameras and within a second image captured by a second camera of the two or more cameras, (ii) identify the point in the second image, (iii) determine a displacement of the point from the first image to the second image, and (iv) determine the depth of pixels for the point based on the displacement.

In an embodiment, the processor is further configured to, when identifying the point in the second image, (i) determine an Epipolar line for the first image and the second image based on the static position of the first camera relative to the second camera, and (ii) search for the point in the second image along the Epipolar line while excluding portions of the second image that do not fall along the Epipolar line.

In another embodiment, the processor is further configured to: (i) associate the set of 3D image data and the set of perspective data with a coordinate system of an image guided surgery system, and (ii) display the set of 3D image data during an image guided surgery navigation procedure based upon the association with the coordinate system.

In an embodiment, (i) the position sensor is configured to produce the set of position signals based on the location and orientation of the endoscope during use, (ii) the set of perspective data indicates the location and orientation of the endoscope during capture of the set of image data, and (iii) the processor is further configured to provide the set of 3D image data and the set of perspective data to an image guided surgery navigation system.

In another embodiment, the processor is further configured to: (i) receive an input from a user defining a perspective relative to the surgical site, (ii) determine a first portion of the set of 3D image data depicting the surgical site from the perspective based on identifying the perspective within the set of perspective data, and (iii) display the first portion of the set of 3D image data on a display.

In yet another embodiment, the processor is further configured to: (i) receive an indirect 3D scan of the surgical site and a set of scan perspective data associated with the indirect 3D scan, (ii) determine a second portion of the indirect 3D scan depicting the surgical site from the perspective based on identifying the perspective within the set of scan perspective data, and (iii) display the first portion of the set of 3D image data and the second portion of the indirect 3D scan on the display simultaneously.

In a further embodiment, (i) the indirect 3D scan of the surgical site includes pre-operatively captured image data, and (ii) the set of 3D image data includes post-operatively captured image data.

In an embodiment, (i) the indirect 3D scan of the surgical site includes pre-operatively captured image data, (ii) the set of 3D image data includes pre-operatively captured image data, and (iii) the processor is further configured to: (A) receive a scan adjustment input from a user, and (B) reconfigure the association between the indirect 3D scan of the surgical site and the set of scan perspective data based on the scan adjustment input.

There is additionally provided, in accordance with an embodiment of the present invention, a method for three-dimensional (3D) imaging including deploying a distal tip of an endoscope to a surgical site of a patient, the distal tip including: (i) an imaging module operable to capture image data of the surgical site, wherein captured image data includes one or more two-dimensional (2D) images, and (ii) a position sensor proximate to the distal tip and configured to produce position signals based on the location of the endoscope. A set of image data is received from the imaging module and a set of position signals from the position sensor. A set of perspective data is determined based on the set of position signals, wherein the set of perspective data indicates the location of the endoscope during capture of each of the one or more 2D images. An image depth analysis is performed to determine a set of 3D characteristics for each of the one or more 2D images, wherein the set of 3D characteristics includes a depth of pixels. A set of 3D image data is created based on the one or more 2D images and the set of 3D characteristics, and the set of perspective data is associated with the set of 3D image data, wherein the image depth analysis includes a technique selected from the group consisting of: (i) a wavefront sampling technique performed on a single image of the one or more 2D images, and (ii) a passive stereo vision technique performed on a set of two images of the one or more 2D images, wherein each of the set of two images are associated with the same perspective data.

Another embodiment of the present invention provides an image guided surgery (IGS) navigation system including a processor, a memory, and a display, the processor configured to: (a) receive a set of image data produced by a tracked endoscope, the set of image data including one or more two-dimensional (2D) images; (b) receive a set of perspective data produced by the tracked endoscope, wherein the set of perspective data indicates a location of the tracked endoscope during capture of the set of image data; (c) perform an image depth analysis to determine a set of 3D characteristics of the set of image data, wherein the set of 3D characteristics includes a depth of pixels in the one or more 2D images; (d) create a set of 3D image data based on the one or more 2D images and the set of 3D characteristics; (e) associate the set of perspective data with the set of 3D image data; and (f) cause the display to show the set of 3D image data from a selected perspective based on the set of perspective data including the selected perspective.

The present invention will be more fully understood from the following detailed description of the embodiments thereof, taken together with the drawings in which:

Figure 2:
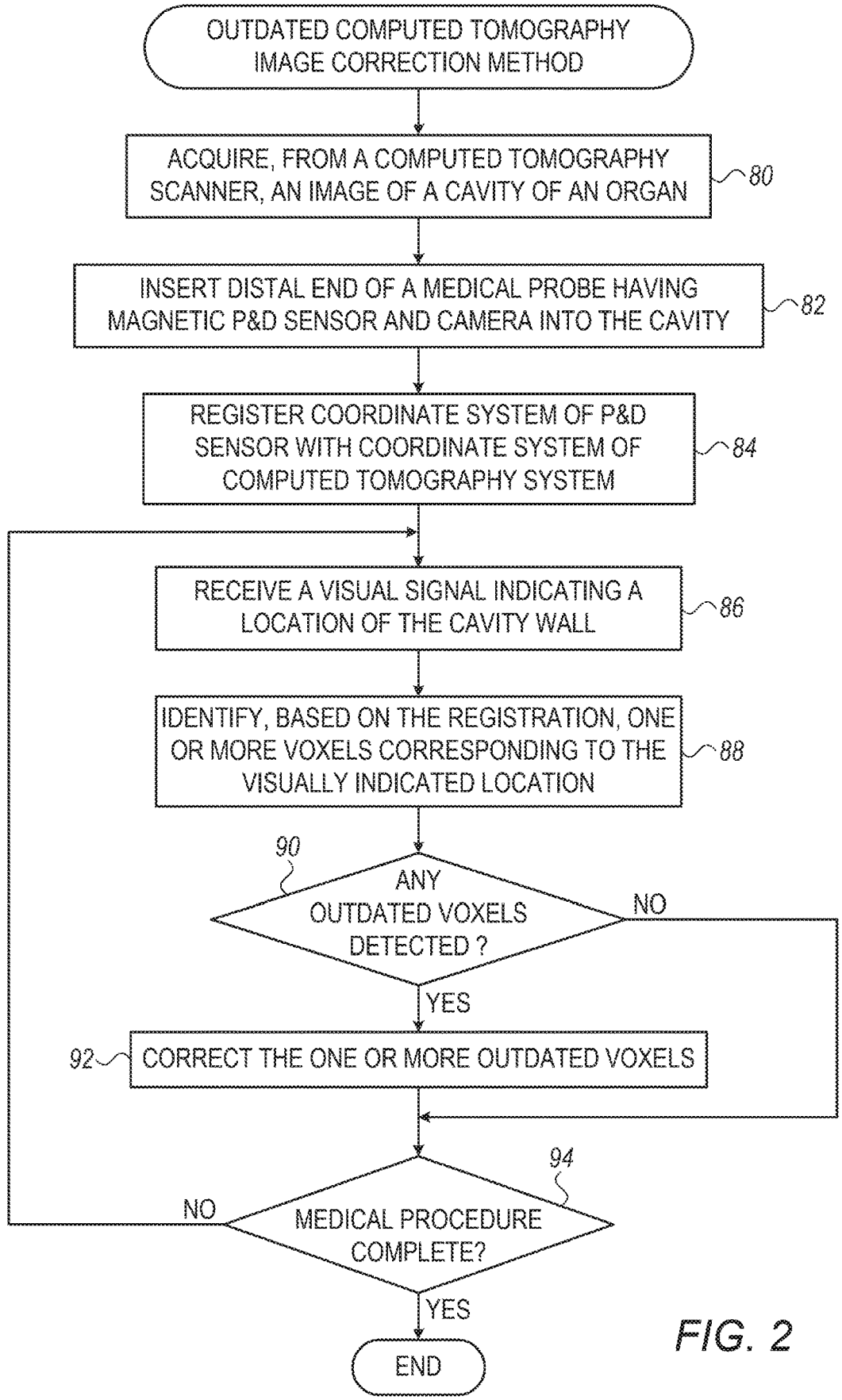
Figure 3:
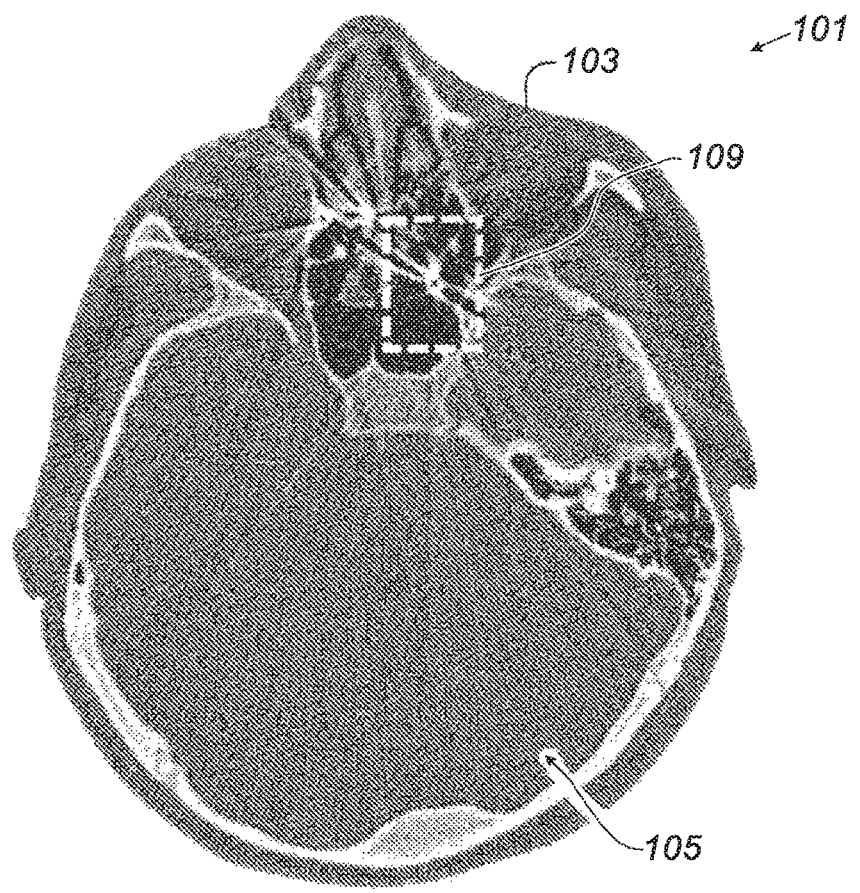
Figure 4:
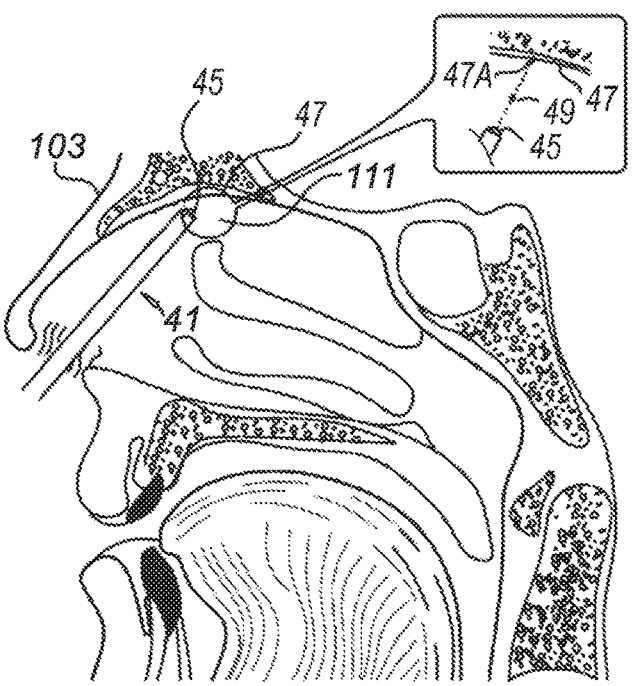
Figure 5:
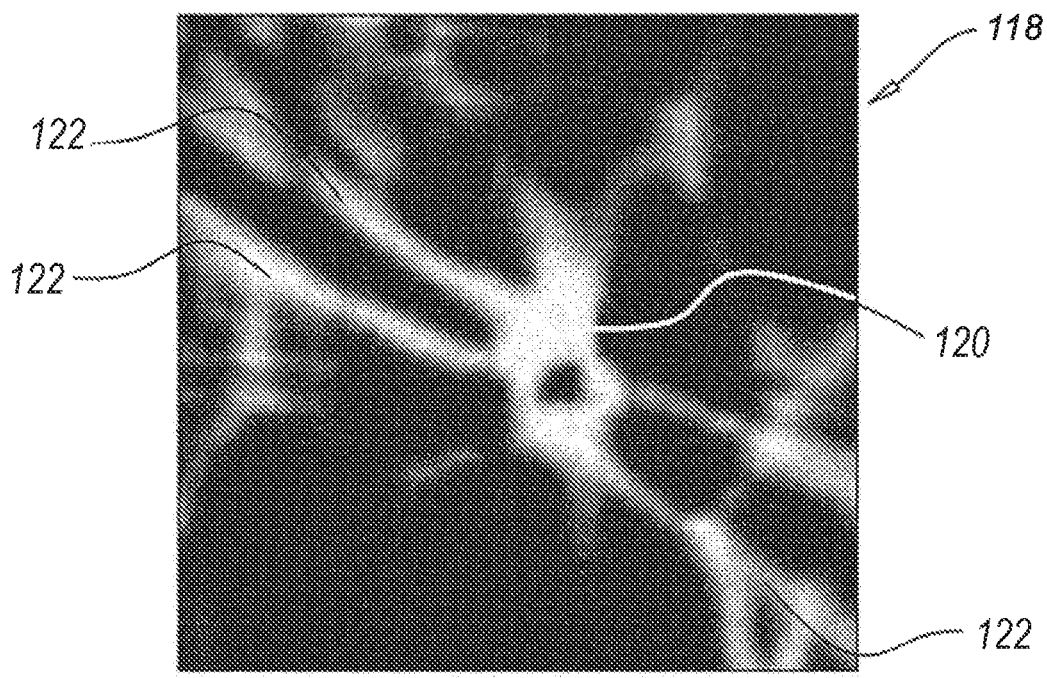
Figure 6:
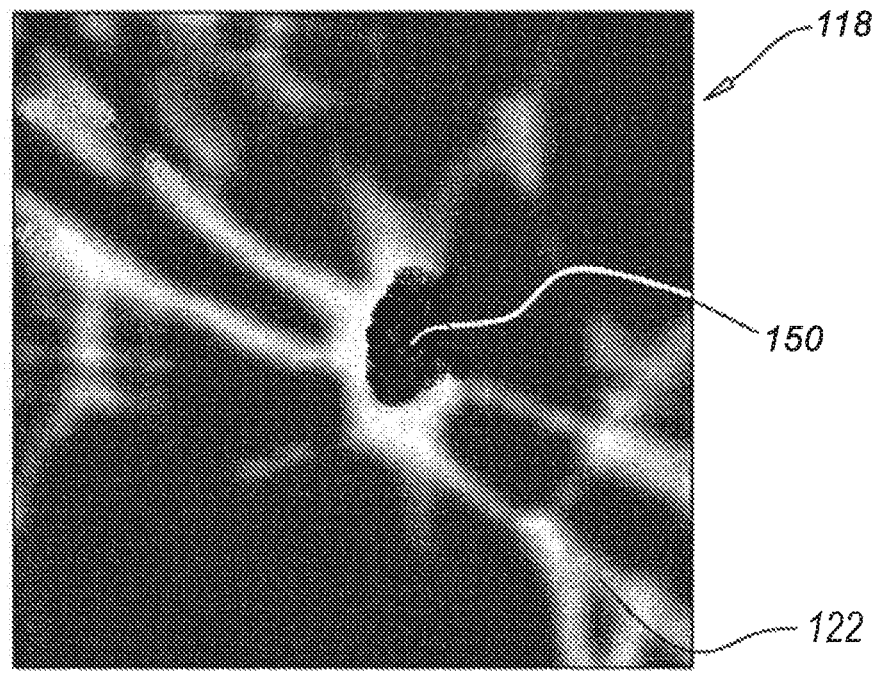
Figure 7:
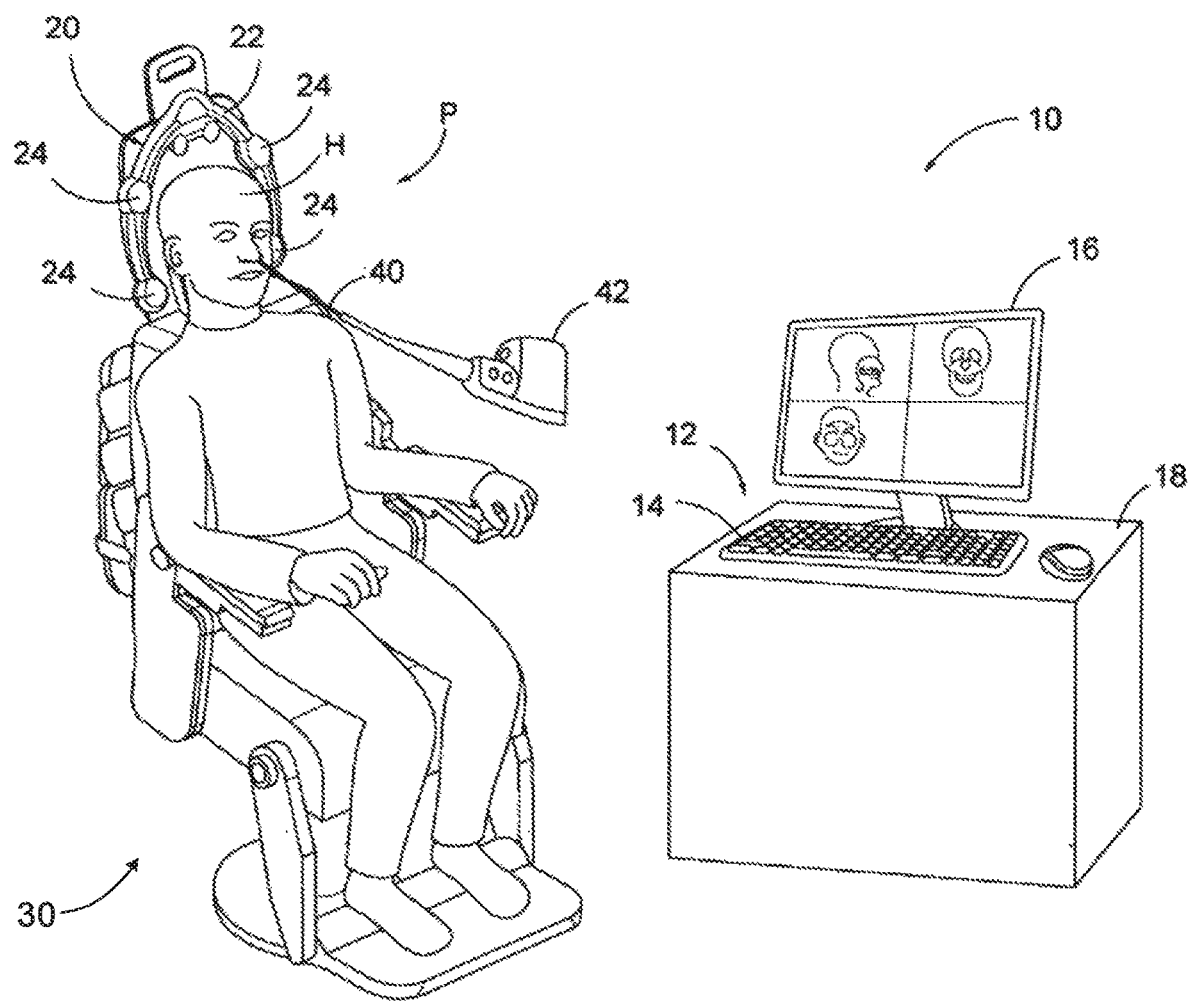
Figure 8:
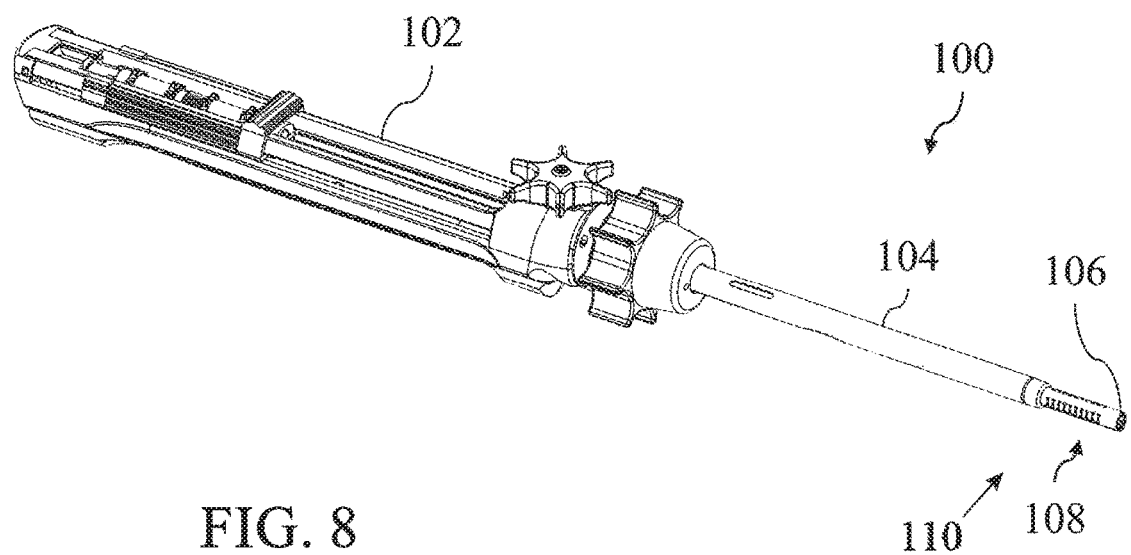
Figure 9A:
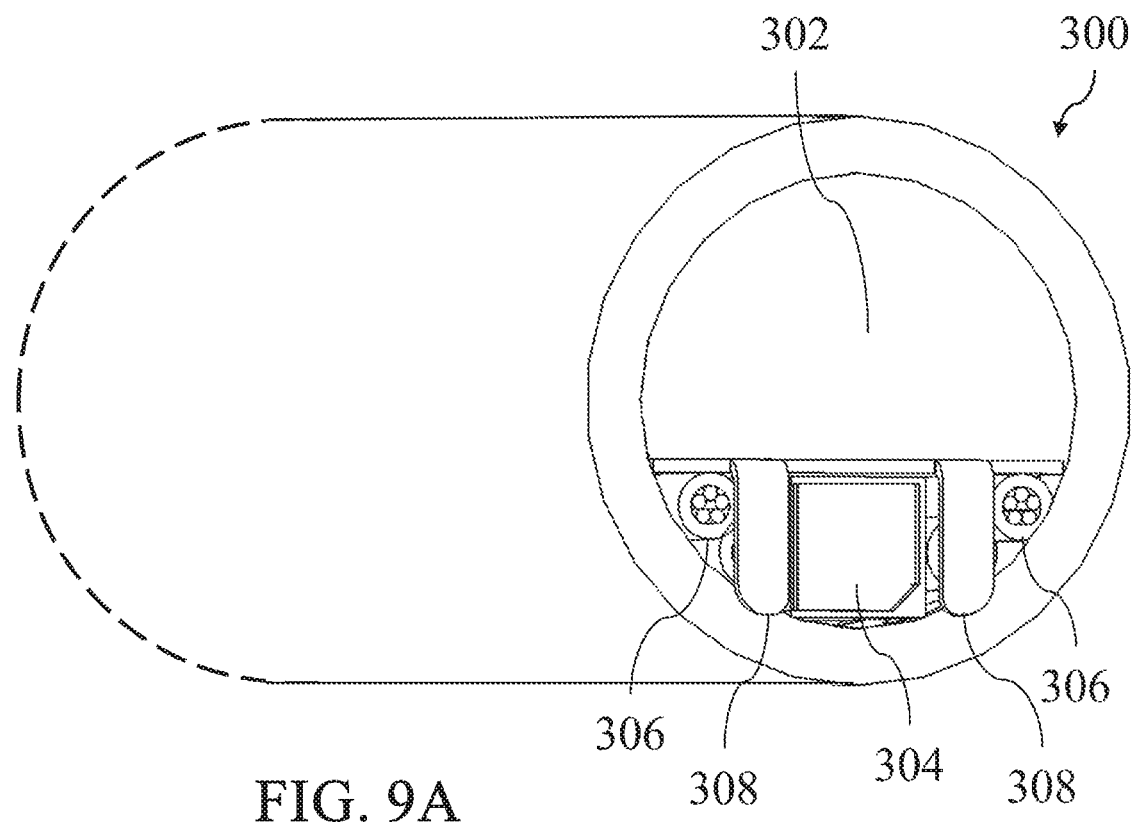
Figure 9B:
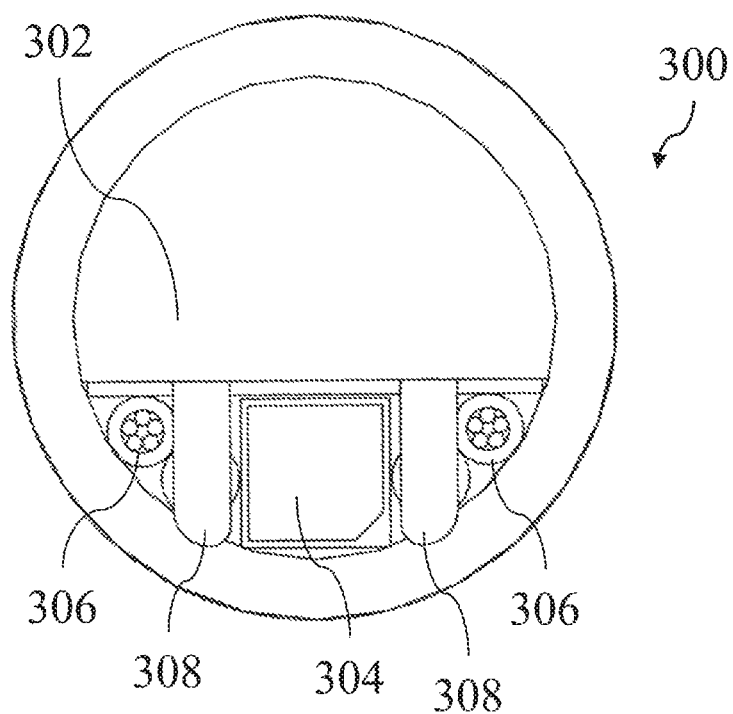
Figure 10A:
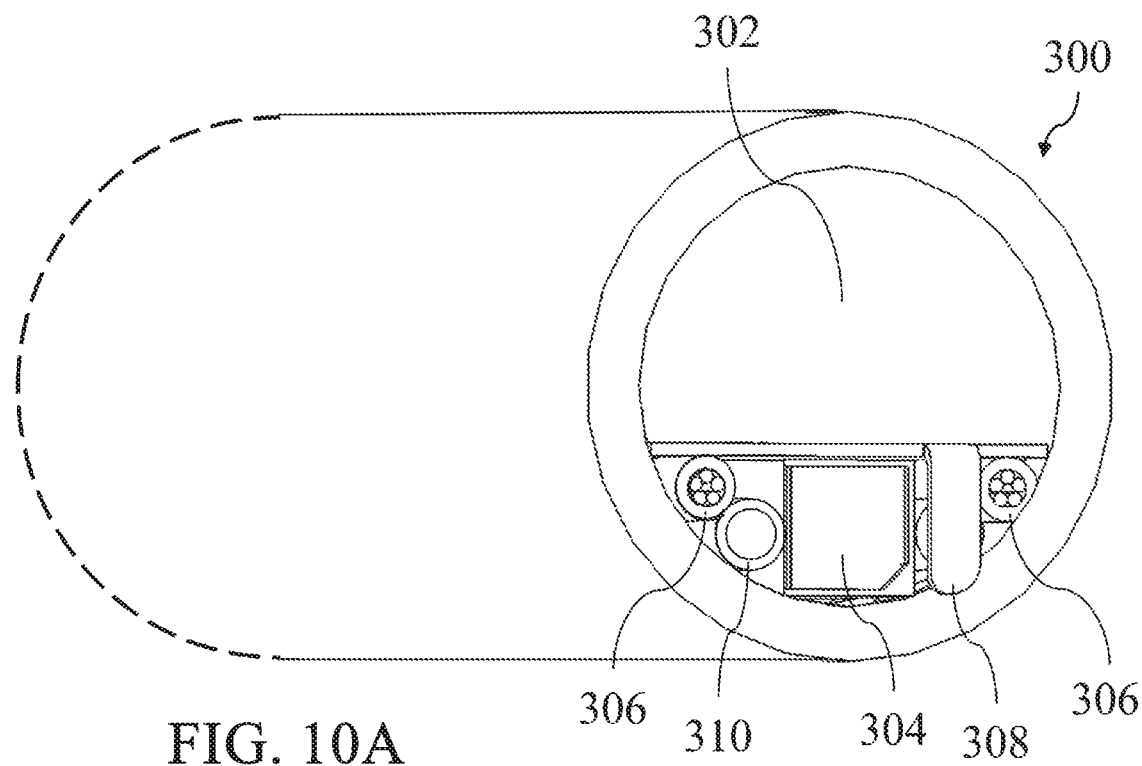
Figure 10B:
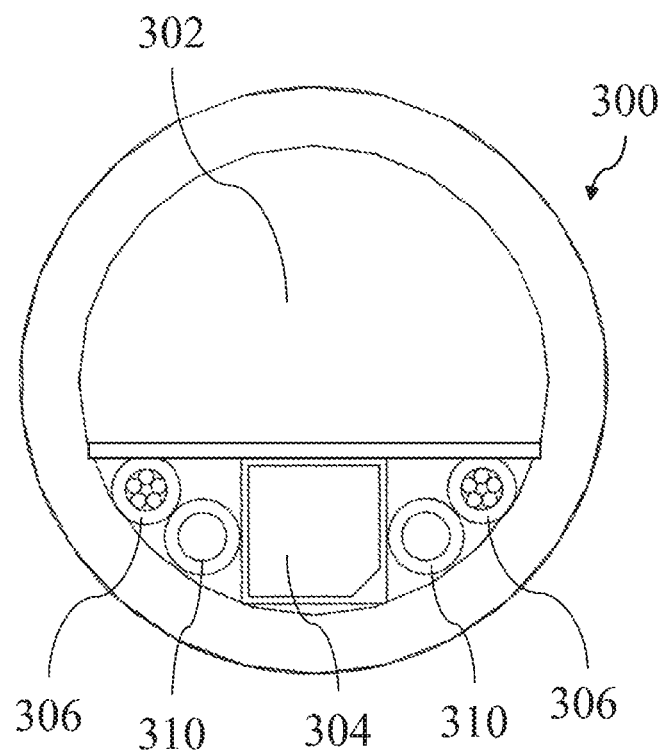
Figure 11:
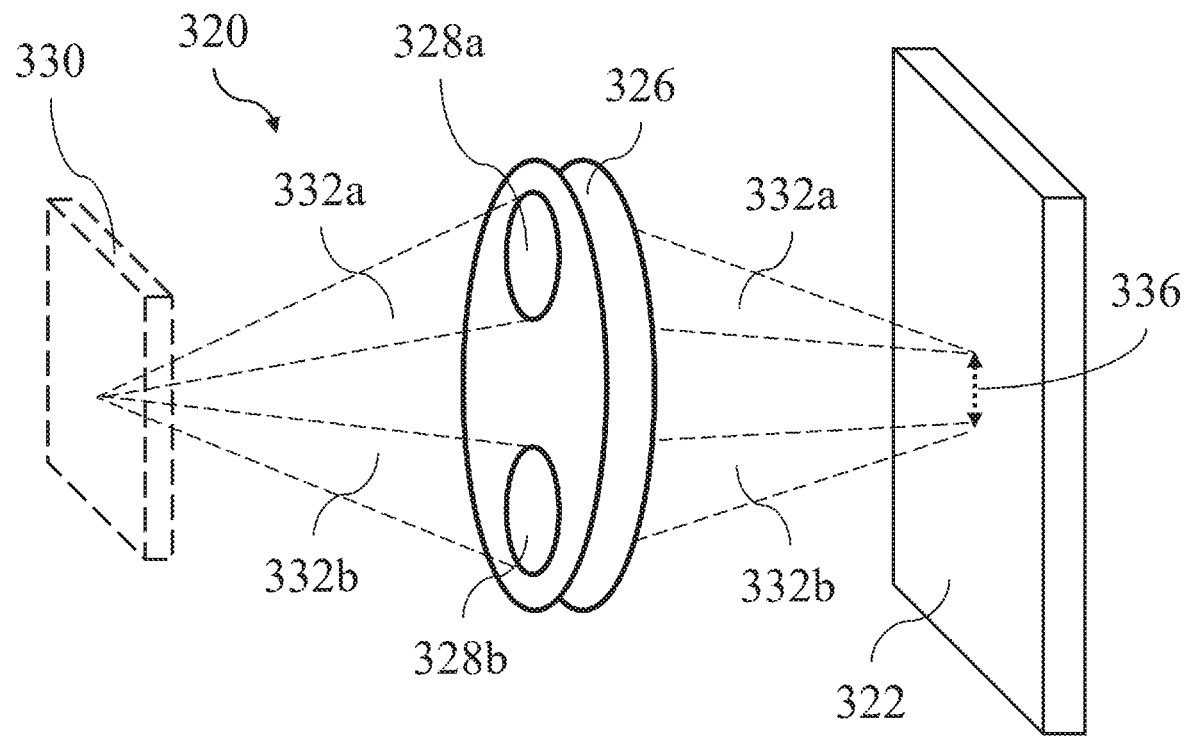
Figure 12:
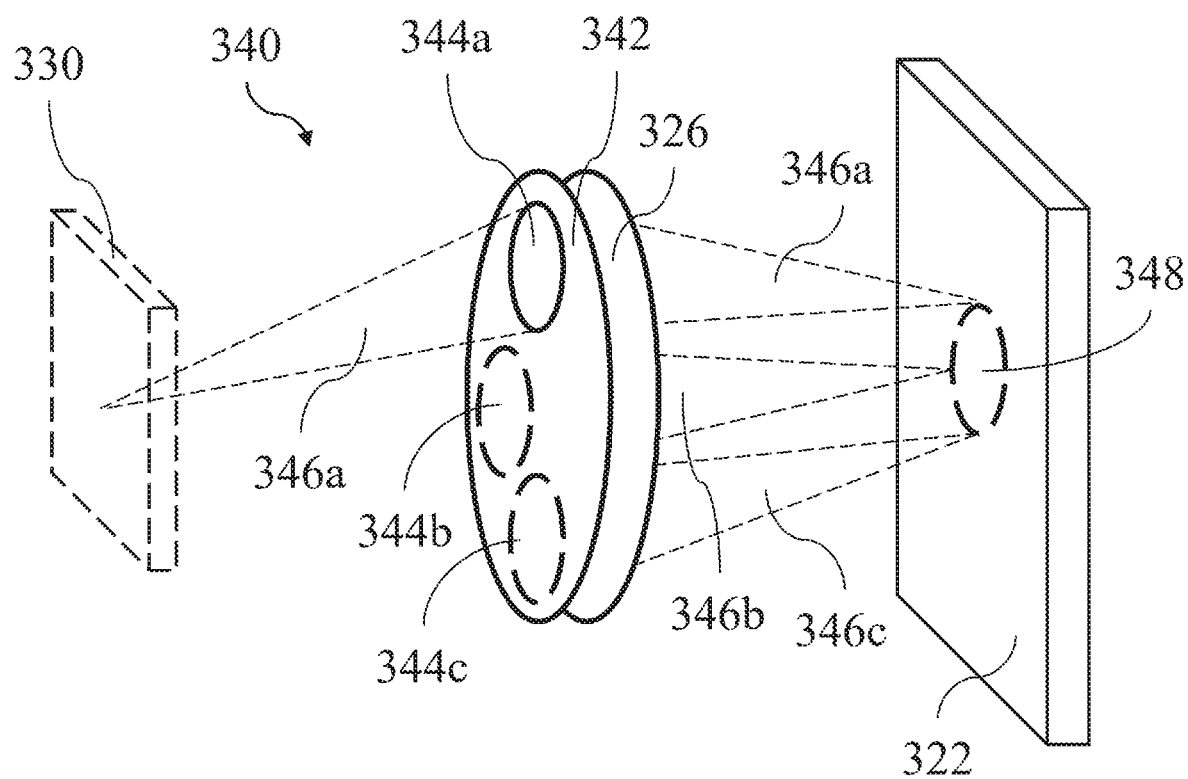
Figure 13:
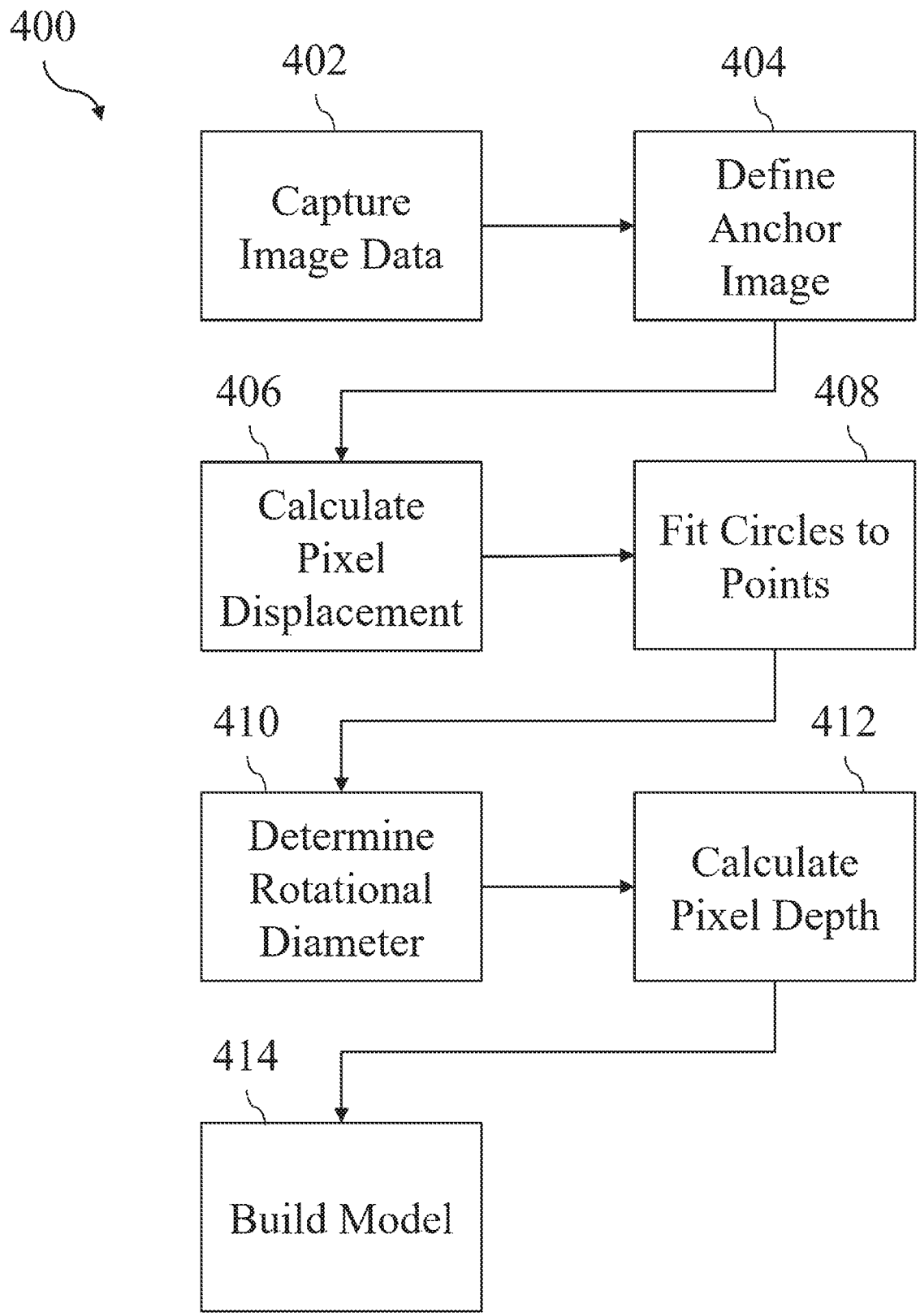
Figure 14A:
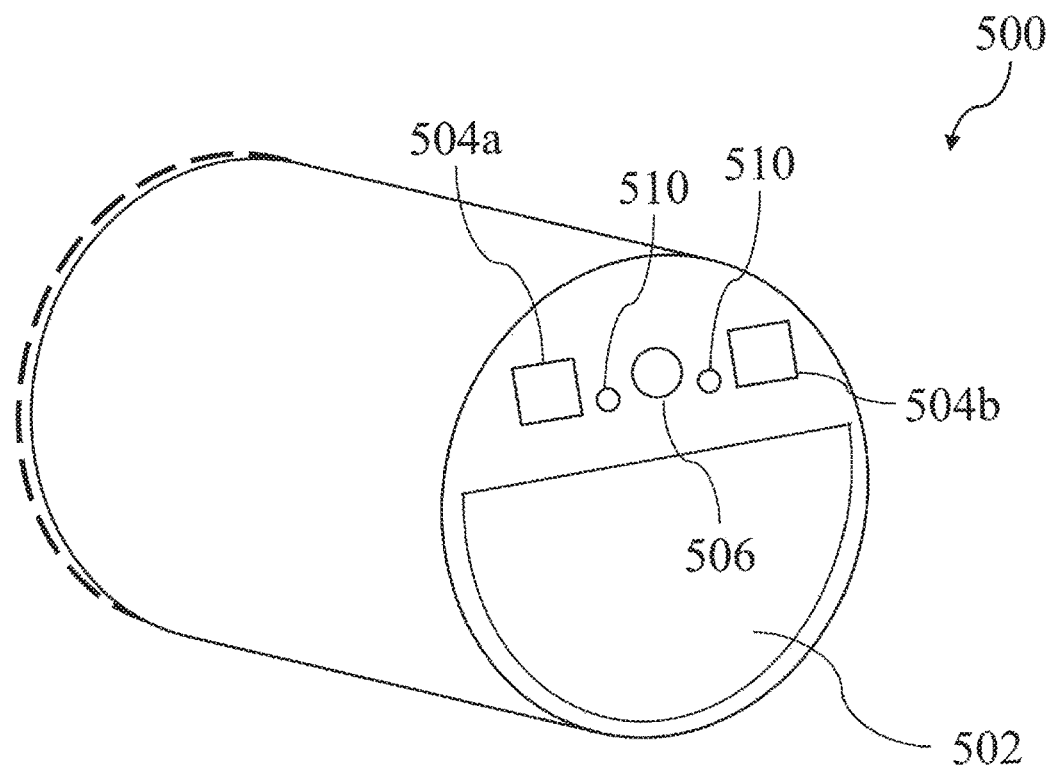
Figure 14B:
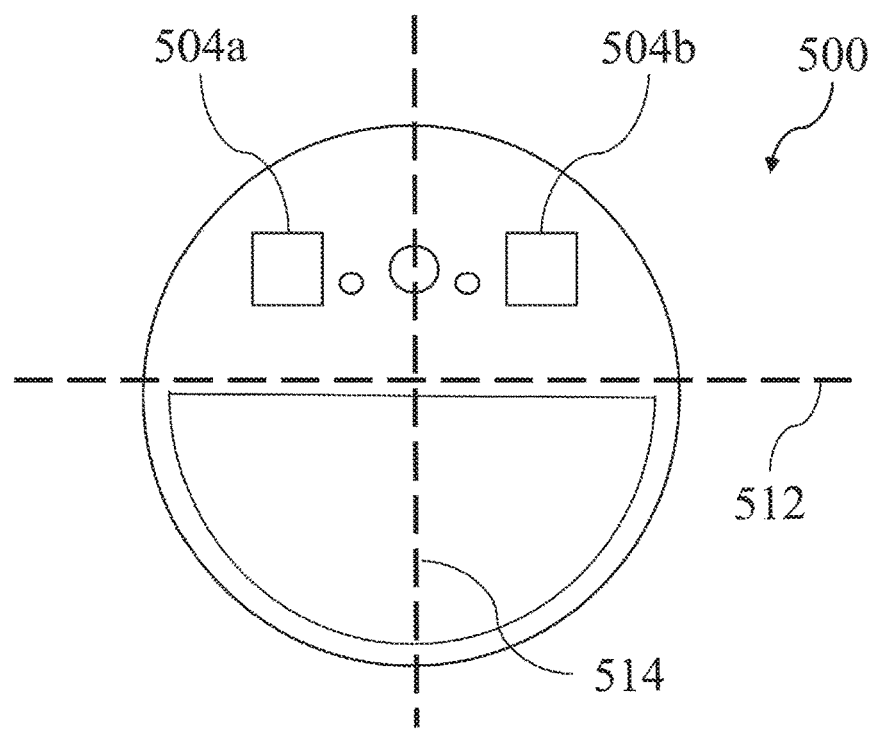
Figure 15A:
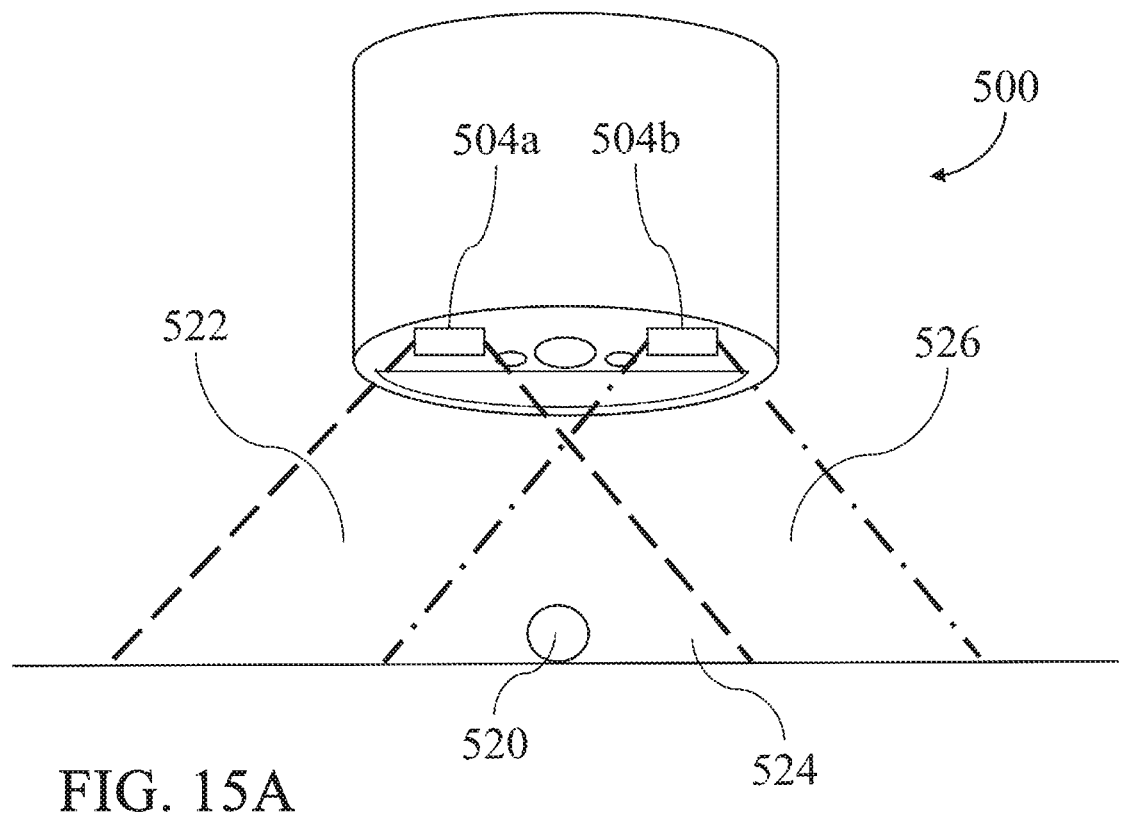
Figure 15B:
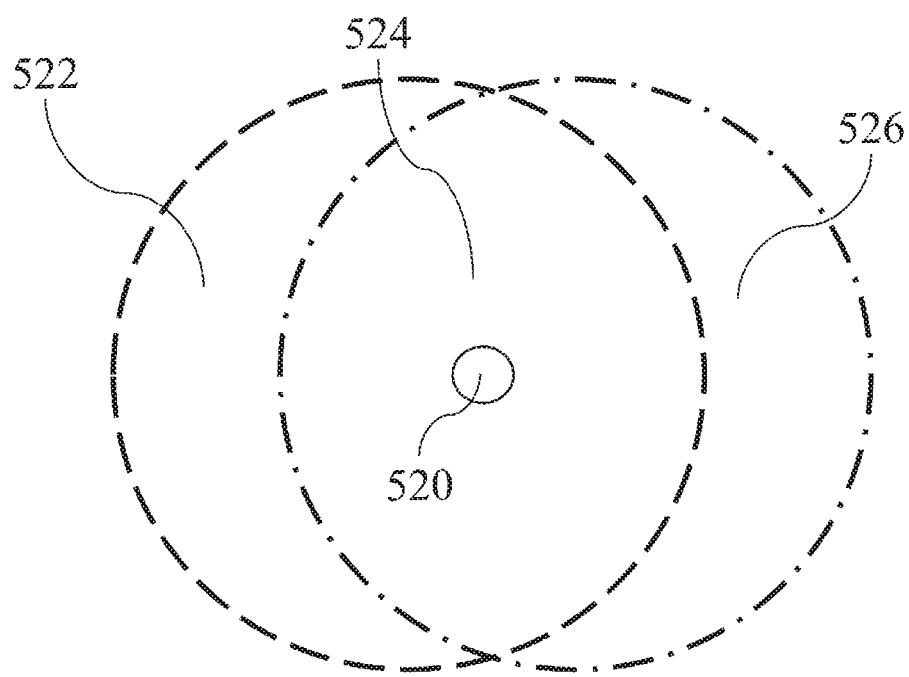
Figure 16:
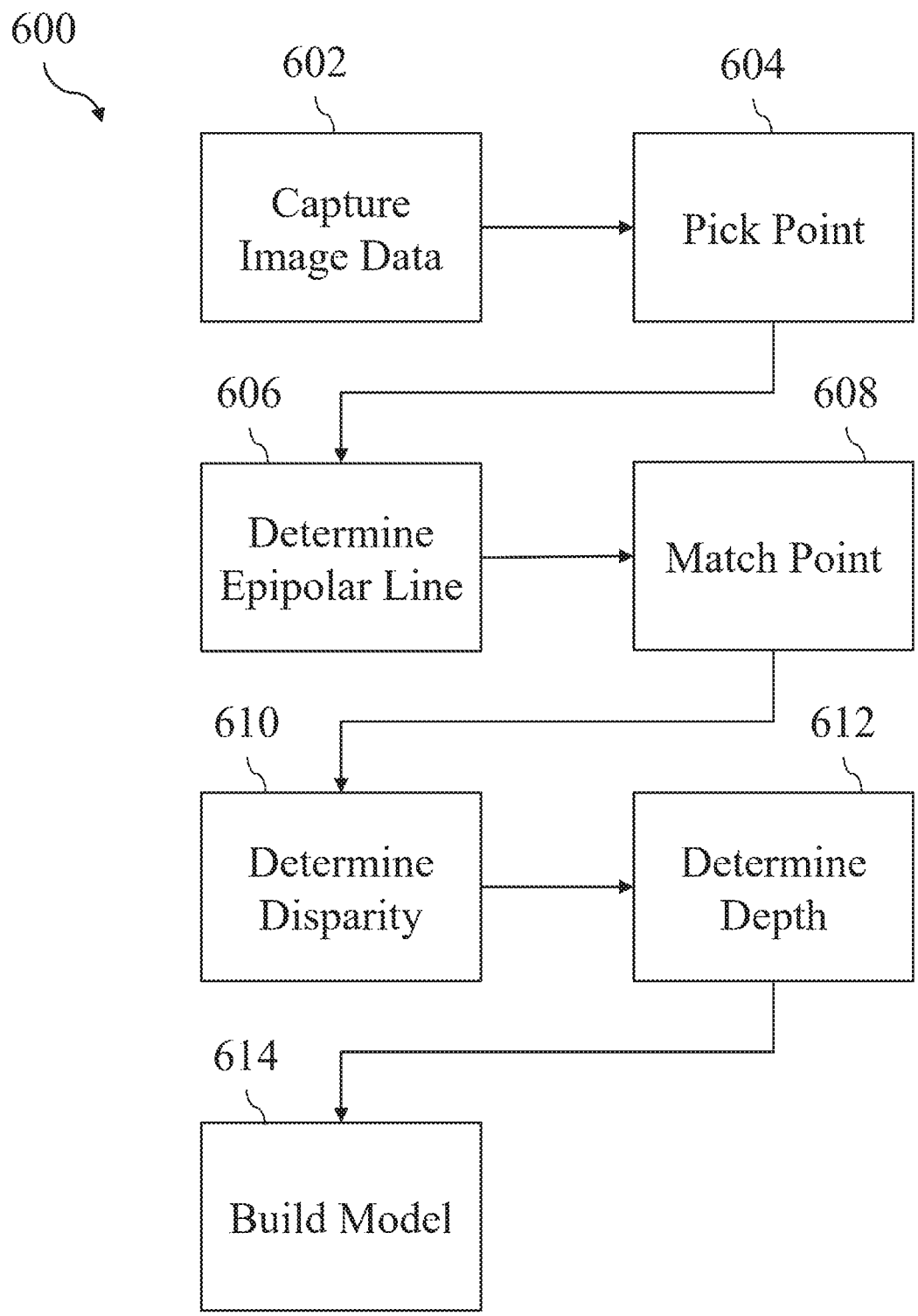
Figure 17:
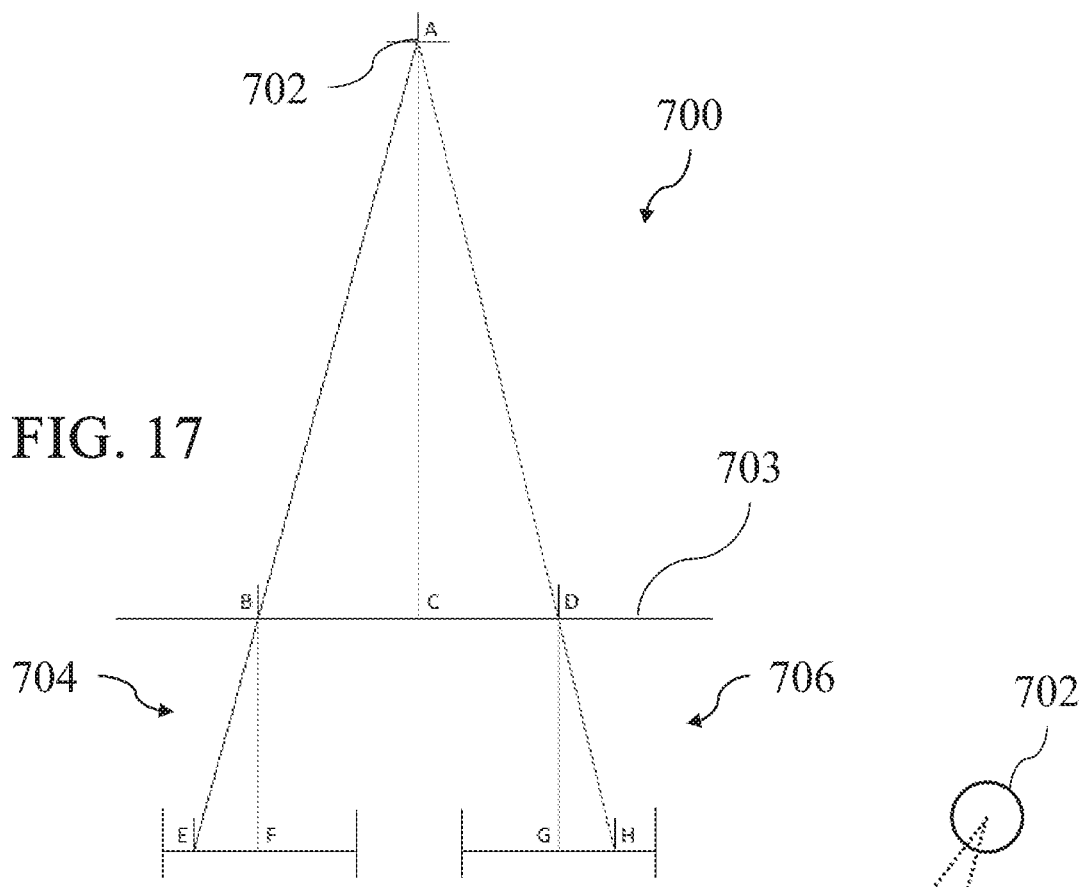
Figure 18:
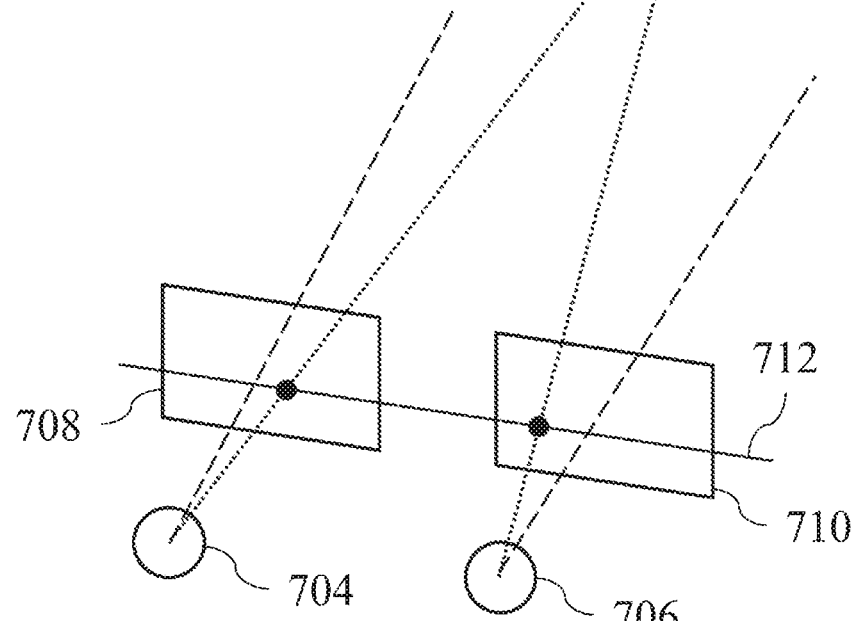
Figure 19:
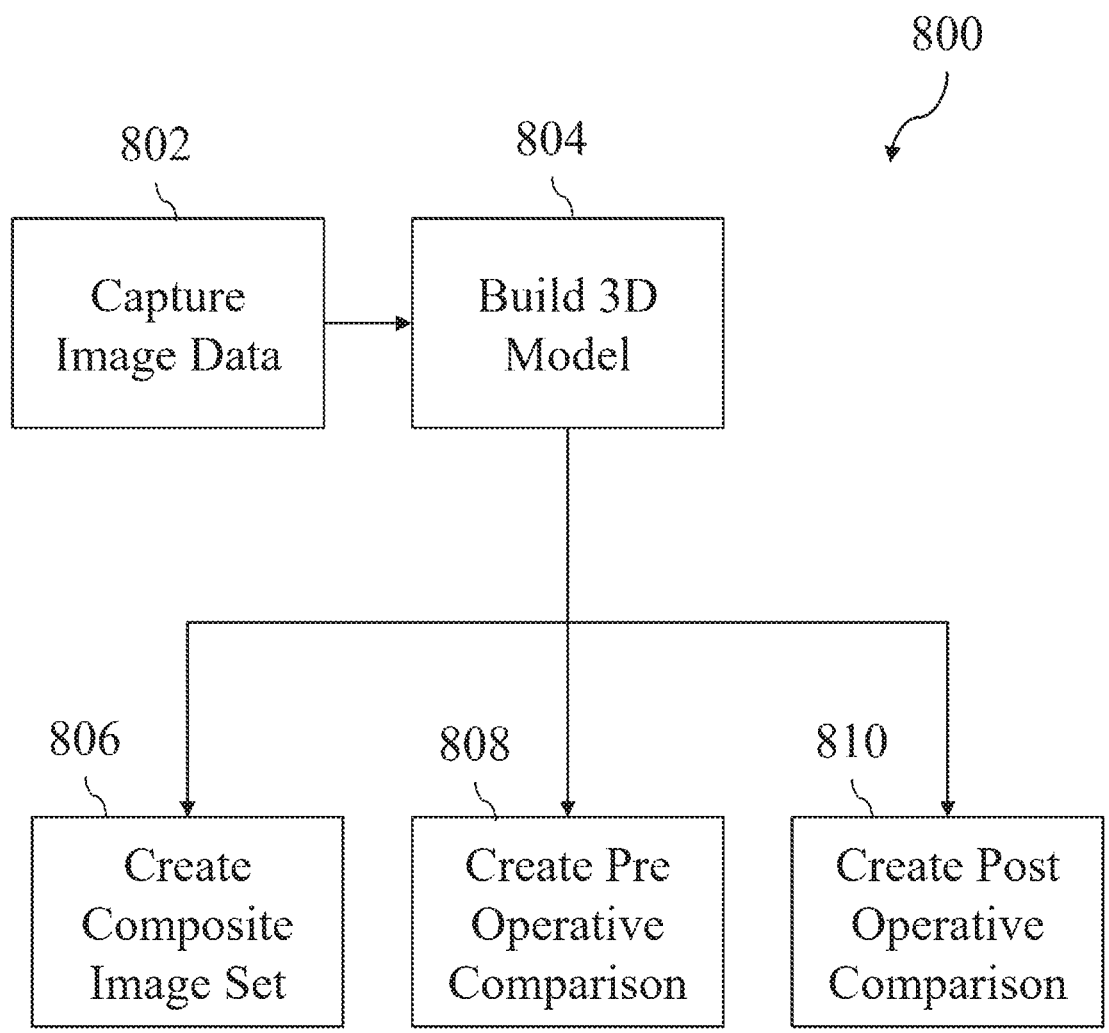

image while performing an invasive medical procedure, in accordance with an embodiment of the present invention;

FIG. 2 is a flow chart that schematically illustrates a method of correcting an outdated CT image, in accordance with an embodiment of the present invention;

FIG. 3 is a schematic pictorial illustration showing an image slice of a three-dimensional CT image, in accordance with an embodiment of the present invention;

FIG. 4 is a schematic detail view showing a distal end of a probe inserted into a sinus cavity, in accordance with an embodiment of the present invention;

FIG. 5 is a schematic pictorial illustration showing a region of interest of the CT image slice of FIG. 3 prior to updating the CT image, in accordance with an embodiment of the present invention;

FIG. 6 is a schematic pictorial illustration showing the region of interest of the CT image slice of FIG. 5 subsequent to updating the CT image, in accordance with an embodiment of the present invention;

FIG. 7 depicts a schematic view of an exemplary surgery navigation system being used on a patient seated in an exemplary medical procedure chair, in accordance with another embodiment of the present invention;

FIG. 8 depicts a perspective view of an exemplary instrument usable with the surgery navigation system of FIG. 7, in accordance with an embodiment of the present invention;

FIG. 9A depicts a perspective view of an exemplary distal tip of the instrument of FIG. 8 having a single imaging device, in accordance with an embodiment of the present invention;

FIG. 9B depicts an elevation view of the distal tip of FIG. 9A, in accordance with an embodiment of the present invention;

FIG. 10A depicts a perspective view of the distal tip of FIG. 9A with an irrigation diverter removed to show an irrigation channel, in accordance with an embodiment of the present invention;

FIG. 10B depicts an elevation view of the distal tip of FIG. 9A with an irrigation diverter removed to show an irrigation channel, in accordance with an embodiment of the present invention;

FIG. 11 depicts a schematic diagram of an exemplary static sampling aperture configuration for the imaging device of FIG. 9A, in accordance with an embodiment of the present invention;

FIG. 12 depicts a schematic diagram of an exemplary active sampling aperture configuration for the imaging device of FIG. 9A;

FIG. 13 depicts a set of exemplary steps that may be performed to produce a three-dimensional image model using the imaging device of FIG. 9A, in accordance with an embodiment of the present invention;

FIG. 14A depicts a perspective view of an exemplary alternative distal tip of the instrument of FIG. 8 having a set of imaging devices;

FIG. 14B depicts an elevation view of the distal tip of FIG. 14A, in accordance with an embodiment of the present invention;

FIG. 15A depicts a side diagrammatic view of an exemplary set of overlapping fields of view of the set of imaging devices of FIG. 14A, in accordance with an embodiment of the present invention;

FIG. 15B depicts a top-down diagrammatic view of the set of overlapping fields of view of FIG. 14A, in accordance with an embodiment of the present invention;

FIG. 16 depicts a set of exemplary steps that may be performed to produce a three-dimensional image model using the set of imaging devices of FIG. 14A, in accordance with an embodiment of the present invention;

FIG. 17 depicts a diagram illustrating a relationship between disparity and depth in stereo imaging;

FIG. 18 depicts a diagram illustrating an epipolar line in stereo imaging, in accordance with an embodiment of the present invention; and FIG. 19 depicts a flowchart of a set of steps that may be performed to produce and use a three-dimensional image model with the surgery navigation system of FIG. 7.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION OF EMBODIMENTS

Overview

According to one aspect of the present invention, an intra-operative medical imaging system, such as a computerized tomography (CT) imaging system, is a modality typically unavailable in clinics that perform ear, nose and throat (ENT) procedures. Therefore, an ENT physician performing a procedure usually relies on previously acquired medical images such as CT images. The CT images can be used to generate a real-time guide (i.e., a "map") that enables the physician performing the ENT medical procedure to navigate a medical probe within a volume of interest inside a cavity in the head of a patient.

However, in some cases, for example, during or after a surgical ENT procedure, such as shaving an obstructing cartilage or bone at a wall of the cavity, the CT image no longer reflects the true anatomy of the cavity.

Embodiments of the present invention that are described hereinafter provide systems and methods for updating an outdated medical image such as an outdated CT image of a cavity of an organ of a patient, the CT image also being referred to herein as a three-dimensional image.

In some embodiments, during an updating procedure, a camera located at a distal tip of a medical probe and operating in a probe coordinate system visualizes locations inside a cavity comprising open space and organ tissue. A processor estimates the locations using visualization from different positions and directions that the camera provides. The different positions and directions are derived by the processor from signals received from a position and direction (P&D) sensor installed at a distal tip of the medical probe.

Using a multi-view triangulation model, the processor reconstructs the visualized locations by reconstructing distances of the locations from the camera. Such multi-view triangulation model can use, for example, a MATLAB® function named "triangulateMultiview," which returns locations of 3D world points that correspond to points matched across multiple images taken with a P&D calibrated camera.

In order for the CT images to reflect an up to date visualized (i.e., true) anatomy of the cavity, the processor registers the coordinate system associated with the CT imaging system with the coordinate system associated with the medical probe (e.g., with the sensor coordinate system).

The registration enables the processor to identify one or more voxels in the three-dimensional image at the indicated locations, and when the identified voxels have density values in the received three-dimensional image that do not correspond to the newly formed open space (formed, for example, by an ENT shaving procedure) as visualized by the camera, and as estimated by the processor using the multi-view triangulation model, the density values of the identified voxels are updated to correspond to the new open space.

Medical imaging systems typically use different visual effects to present open space and body tissue. For example, a CT system may present open space in black, hard body tissue in white and soft body tissue in (various shades of) gray. Since the camera, being located at the distal edge of the medical probe, can only optically image wall tissue through open space, systems implementing embodiments of the present invention can correct, in an updated three-dimensional (3D) CT image, any optically imaged locations of the cavity that are not presented as open space. In addition, if the camera has entered a location that was not previously open space, embodiments of the present invention can also present the entered location as open space in the updated 3D image.

Other aspects of the disclosed invention provide imaging techniques, such as wavefront sampling and passive stereo vision, that are used to produce 3D image data and 3D models from single camera and multi camera 2D imaging systems. Such techniques are implemented to produce 3D capable imaging systems with small size and low complexity compared to 3D imaging systems with independent dynamically focused cameras. With reduced size and power requirements, such imaging techniques (e.g., systems) are implemented at a distal tip of a surgical instrument having a static or flexible shaft, and may be used to produce 3D imaging of surgical sites within the human body. Such 3D imaging may be used to produce composite image sets usable during IGS navigation, to provide comparisons of pre-operative image sets, and to provide comparisons of post-operative image sets.

In some embodiments, a 3D endoscopy imaging system is provided, which comprise (a) an endoscope comprising a position sensor, and an imaging module positioned at the distal tip of the endoscope and operable to capture a set of image data of the surgical site, wherein the set of image data comprises one or more two-dimensional (2D) images, and (b) a processor communicatively coupled with the endoscope and configured to:

(i) receive the set of image data and the set of position signals from the endoscope, (ii) determine a set of perspective data based on the set of position signals, wherein the set of perspective data indicates the location of the endoscope during capture of each of the one or more 2D images, (iii) perform an image depth analysis to determine a set of 3D characteristics for each of the one or more 2D images, wherein the set of 3D characteristics comprises a depth of pixels, (iv) create a set of 3D image data based on the one or more 2D images and the set of 3D characteristics, and (v) associate the set of perspective data with the set of 3D image data;

wherein the image depth analysis comprises a technique selected from the group consisting of:

(i) a wavefront sampling technique performed on a single image of the one or more 2D images, and (ii) a passive stereo vision technique performed on a set of two images of the one or more 2D images, wherein each of the set of two images are associated with the same perspective data.

Embodiments of the present invention disclose medical image, such as CT image, correction using a P&D tracking assisted visualization technique of cavity locations. Using the embodiments may eliminate the need for repeating an imaging procedure, such as a CT imaging procedure, typically requiring a large and expensive operation facility.

CT Image Correction Using P&D Tracking Assisted Optical Visualization

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

Figure 1A:
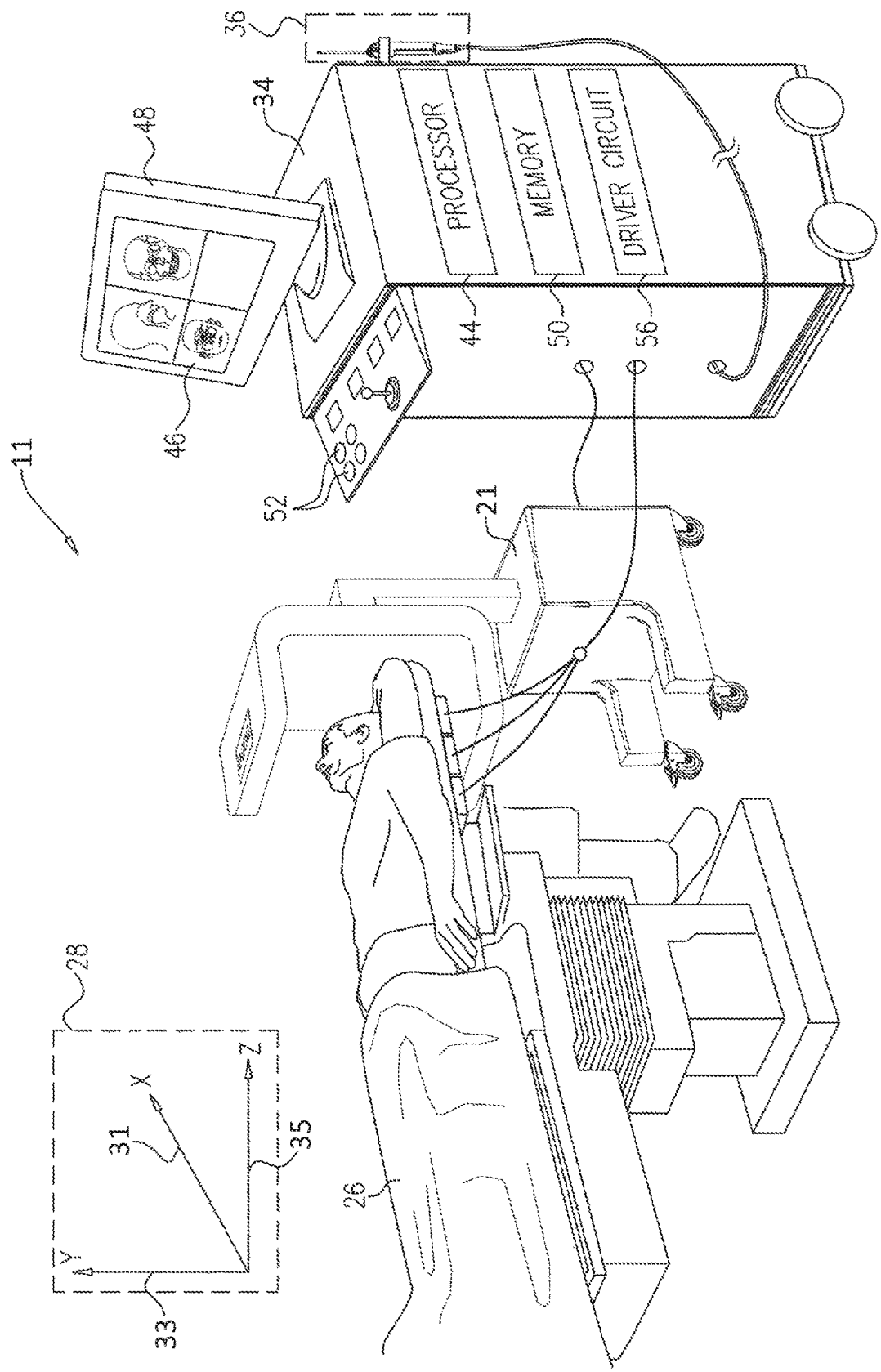
FIGS. 1A and 1B, referred to collectively as FIG. 1, are schematic pictorial illustrations of a medical system configured to correct an outdated computerized tomography (CT)
Figure 1B:
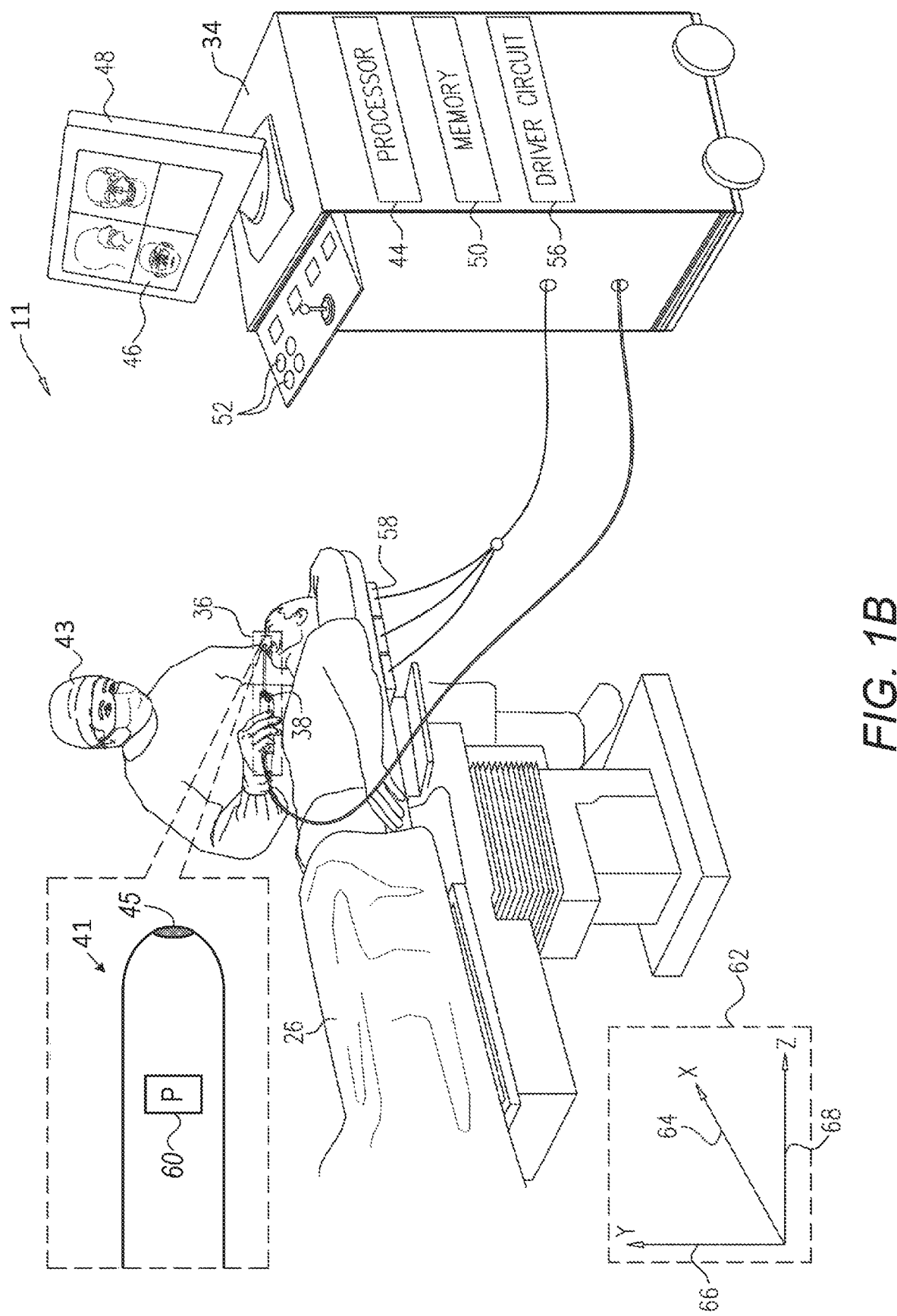

FIGS. 1A and 1B, referred to collectively as FIG. 1, are schematic pictorial illustrations of a medical system 11 configured to correct an outdated computerized tomography (CT) image while performing an invasive medical procedure, in accordance with an embodiment of the present invention. In the example shown in FIG. 1, medical system 11 comprises a medical imaging system comprising a mobile CT scanner 21, a control console 34, and a medical probe 36. In embodiments described herein, it is assumed that medical probe 36 is used for ENT diagnostic or therapeutic treatment, such as minimally invasive catheter-based sinus surgery on a patient 26. Alternatively, medical probe 36 may be used, mutatis mutandis, for other therapeutic and/or diagnostic purposes.

As shown in FIG. 1A, prior to performing an invasive medical procedure on patient 26, CT scanner 21 generates electrical signals comprising image data for a lumen (e.g., a nasal cavity or a paranasal sinus) of the patient, and conveys the generated image data to control console 34. Computed tomography scanner 21 generates the image data in an image coordinate system 28 comprising an X-axis 31, a Y-axis 33 and a Z-axis 35.

As shown in FIG. 1B, medical probe 36 comprises a handle 38 that an operator 43 can grasp and manipulate in order to insert a distal end 41 of the medical probe into a lumen, such as a nasal cavity or a paranasal sinus, of patient 26.

Distal end 41 comprises a camera 45 generating image data in response to a scene viewed by the camera. Distal end 41 also comprises a magnetic field sensor 60, which, as described below, generates signals providing the position and orientation of the distal end. In the configuration shown in FIG. 1, control console 34 comprises a processor 44 that converts the image data received from camera 45 into an image 46, and presents the image as information regarding the medical procedure on a display 48.

Based on the signals received from medical probe 36 and other components of medical system 20, control console 34 drives display 48 to update image 46 in order to present a current position of distal end 41 in the patient's head, as well as status information and guidance regarding the medical procedure that is in progress. Processor 44 stores data representing image 46 in a memory 50. In some embodiments, operator 40 can manipulate image 46 using one or more input devices 52.

Processor 44 typically comprises a general-purpose computer, with suitable front end and interface circuits for receiving signals from medical probe 36 and controlling the other components of control console 34. Processor 44 may be programmed in software to carry out the functions that are described herein. The software may be downloaded to control console 34 in electronic form, over a network, for example, or it may be provided on non-transitory tangible media, such as optical, magnetic or electronic memory media. Alternatively, some or all of the functions of processor 44 may be carried out by dedicated or programmable digital hardware components.

In embodiments described herein, medical system 11 uses magnetic position sensing to determine position and direction coordinates of distal end 41 of medical probe 36 inside patient 26. To implement magnetic based position and direction sensing, control console 34 comprises a driver circuit 56 which drives field generators 58 to generate magnetic fields within the probed organ of patient 26. Typically, field generators 58 comprise coils, which are placed below the patient at known positions external to patient 26. These coils generate magnetic fields in a predefined working volume that contains a lumen such as a paranasal sinus. Magnetic field sensor 60 (also referred to herein as position and direction (P&D) sensor 60) within distal end 41 of medical probe 36 generates electrical signals in response to the magnetic fields from the coils, thereby enabling processor 44 to determine the position and the direction of distal end 41 within the working volume.

Magnetic position tracking techniques are described, for example, in U.S. Pat. Nos. 5,391,199, 6,690,963, 5,443,489, 6,788,967, 5,558,091, 6,172,499 and 6,177,792, whose disclosures are incorporated herein by reference. The signals generated by magnetic field sensor 60 indicate the current location of distal end 41 in a sensor coordinate system 62 defined by the positions of generators 58, and system 62 is assumed to comprise an X-axis 64, a Y-axis 66 and a Z-axis 68. In the example shown in FIG. 1, X-axis 64 generally corresponds to X-axis 31, Y-axis 66 generally corresponds to Y-axis 33 and Z-axis 68 generally corresponds to Z-axis 35. Such systems and techniques are similar or the same as those described in connection with other aspects of the invention described in connection with FIG. 7.

In embodiments described herein, medical system 11 uses camera 45 to image portions of a cavity. The positions from which camera 45 is imaging the cavity, as well as the respective directions the camera is aiming at are derived using sensor 60, as described above. Based on the P&D tracking and using a multi-view triangulation model, processor 44 is able to determine (i) a location of portions of the walls of the cavity wherein the distal end is situated, and (ii) locations between the imaged location on the cavity wall and the camera, including camera 45 itself, which are all in open space, and to update the CT images accordingly.

FIG. 2 is a flow chart that schematically illustrates a method of correcting an outdated CT image, and FIGS. 3, 4, 5, and 6 are schematic figures illustrating the method, in accordance with an embodiment of the present invention. In an acquiring step 80, processor 44 acquires image data from CT scanner 21, stores the image data to memory 50, and generates, based on the acquired image data, a three-dimensional image. Step 80 is typically performed prior to the updating CT image procedure to be performed on patient 26.

FIG. 3 is a schematic pictorial illustration showing an image slice 101 of a three-dimensional computed tomography image that may be acquired in step 80. Processor 44 generates image slice 101 in response to receiving the image data from CT scanner 21. In operation, processor 44 typically incorporates image slice 101 into image 46.

In the example shown in FIG. 3, image slice 101 comprises a two-dimensional "slice" of a head 103 of patient 26. As indicated by a legend 106, image slice 101 comprises voxels 105 of the three-dimensional image that correspond to three-dimensional locations in the computed tomography image of head 103. Processor 44 typically presents each given voxel 105 using different a visual effect that corresponds to the density detected at the three-dimensional location corresponding to the given voxel. Examples of densities include, but are not limited to, open space, hard organ tissue and soft organ tissue, and examples of visual effects include, but are not limited to, colors, shadings (e.g., different shades of gray) and patterns (e.g., gradients, pictures, textures, lines, dots and boxes).

As indicated by a legend 107, voxels 105 can be differentiated by appending a letter to the identifying numeral, so that the voxels comprise voxels 105A-105C. In the example shown in FIG. 3, voxels 105A indicate open space and are presented in black, voxels 105B indicate hard organ tissue (e.g., bone) and are presented in white, and voxels 105C indicate soft tissue (e.g., fat, muscle cartilage and brain tissue) and are presented in gray. While embodiments herein describe image slice 101 comprising voxels 105 with three different visual effects (i.e. voxels 105A-105C), presenting the voxels with any number of visual effects representing any number of densities is considered to be within the spirit and scope of the present invention.

Image slice 101 also comprises a region of interest 109. As described in the description referencing FIGS. 5 and 6 hereinbelow, region of interest 109 includes cavity wall 47 locations having an outdated CT value (i.e., density value) that processor 44 can update using embodiments described herein.

Returning to the flowchart, to initiate the updating procedure, operator 43 manipulates handle 38 so that, in an insertion step 82, distal end 41 enters a cavity of an organ of patient 26. It will be understood that there is typically a delay, which may be days or even weeks, between steps 80 and 82.

Next, in a registration step 84, processor 44 registers image coordinate system 28 with sensor 60 coordinate system 62. The registration may be performed by any suitable process known in the art. Upon performing the registration, each three-dimensional position indicated by a signal generated by magnetic field sensor 60 corresponds to one or more voxels in the CT images that were acquired in step 80.

In a receiving visual signal step 86, processor 44 receives visual signals from camera 45 indicating a location of cavity wall 47, and in an identification step 88, the processor uses the registration and the multi-view triangulation model to identify one or more voxels in the CT images that correspond to the indicated location.

FIG. 4 is a schematic detail view showing distal end 41 inserted into a sinus cavity 111. Camera 45 in distal end 41 acquires images of cavity wall 47 from different perspectives as the distal end moves. Based on the visual signals of wall 47 that camera 45 acquires, and, as noted above, using the multi-view triangulation model, processor 44 estimates a location 47A of the cavity wall. It will be understood that any location on the respective line of sight of camera 45 to location 47A, such as location 49, as well as the location of camera 45 itself, has to be an open space inside the cavity.

Returning to the flowchart, in a first comparison step 90, if any of the one or more identified voxels have an outdated CT density value i.e., of tissue instead of a (newly formed by an ENT procedure) open space, then in a correction step 92, processor 44 corrects the outdated voxel(s) values to represent the voxels as a (newly formed) open space. For example, if a given identified voxel has a CT density outdated value corresponding to hard or soft tissue then processor 44 can update the density value to correspond to the open space. If in step 90 none of the one or more identified voxels have an outdated CT value, then the method continues with step 94.

In embodiments of the present invention, updating the one or more updated voxels in an image slice updates the three-dimensional computed tomography image stored in memory 50.

After completion of step 92, control proceeds to a second comparison step 94.

In second comparison step 94, if operator 40 has completed the updating procedure, i.e., the operator has sufficiently inspected cavity 47 or other cavities, then the method ends. However, if operator 40 has not yet completed the updating procedure, then the method continues with step 86.

FIG. 5 is a schematic pictorial illustration showing region of interest 118 of image slice 101 prior to updating the computed tomography image, as is acquired in step 80. In the example shown in FIG. 5, an obstructing bone 120 comprises voxels 105B (i.e., dense bone) surrounding an inner region of voxels 105A (i.e., a hollow region of the bone growth), and voxels 105C comprise soft tissue.

FIG. 6 is a schematic pictorial illustration showing region of interest 118 of image slice 101 subsequent to updating the computed tomography image, i.e., after completion of the steps of the flowchart of FIG. 2. As shown in FIG. 6, region of interest 118 comprises updated regions 150. Regions 150 comprise regions which processor 44 estimated are newly formed open space based on visualization from camera 45 and using the multi-view triangulation model. Regions 150 were formed, for example, by an ENT shaving procedure that removed some of the obscuring bone 120 in FIG. 5.

Display 48 typically presents a subset of voxels 105 that processor 44 can update during an updating procedure using embodiments described herein. As described supra, image slice 101 comprises a two-dimensional "slice" of the three-dimensional image that processor 44 generates in response to receiving the image data from mobile computed tomography scanner 21. Since operator moves distal end 41 in a three-dimensional space (i.e., three-dimensional coordinate systems 28 and 62), it will be understood that there can be additional voxels 105 (i.e., not included in the two-dimensional image slice currently being presented on display 48) whose respective density values are updated by processor 44 in response to detected cavity wall 47 locations by camera 45.

Exemplary Image Guided Surgery Navigation System

According to another aspect of the invention, when performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P).

FIG. 7 shows an exemplary IGS navigation system (10) enabling an ENT procedure to be performed using image guidance, in accordance with an embodiment of the present invention. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pub. No. 2018/0310886, entitled "Apparatus to Secure Field Generating Device to Chair," published Nov. 1, 2018, issued as U.S. Pat. No. 10,561,370 on Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit (e.g., a set of electronic circuits arranged to evaluate and execute software instructions using combinational logic circuitry or other similar circuitry) communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a scan image (e.g., CT, MM, or other X-ray or indirect imaging method) of the patient's head (H), and/or a computer-generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

Endoscope with Single Camera 3D Imaging

FIG. 8 shows an exemplary endoscope (100) usable with a surgery navigation system or other surgical system such as the IGS navigation system (10), in accordance with an embodiment of the present invention. The endoscope (100) includes a body (102) that may be gripped during use. A set of controls (103) are positioned at the distal end of body (102). A shaft (104) extends distally from the body (102). Shaft (104) includes a flex portion (108) and a distal tip (106). As will be described in greater detail below, distal tip (106) may include one or more features such as a camera, a light source, irrigation and suction, and/or channels through which flexible tools may be deployed. The endoscope (100) also includes a position sensor (110) located between flex portion (108) and distal tip (106). Position sensor (110) may comprise one or more coils that are configured to generate position indicative signals in response to an alternating electromagnetic field generated by field generators (24), such that navigation system (10) may track the three-dimensional position of distal tip (106) within the head (H) of the patient (P) in real time, similar to the position tracking of navigation guidewire (40) described above.

Controls (103) are operable to drive rotation of shaft (104) about the longitudinal axis of shaft (104). Controls (103) are also operable to drive deflection of distal tip (106) away from the longitudinal axis of shaft (104) at flex portion (108). By way of example only, controls (103) may be configured and operable in accordance with at least some of the teachings of U.S. Pub. No. 2019/0015645, entitled "Adjustable Instrument for Dilation of Anatomical Passageway," published Jan. 17, 2019, issued as U.S. Pat. No. 10,874,839 on Dec. 29, 2020, the disclosure of which is incorporated by reference herein. By way of further example only, endoscope (100) may also include one or more controls for activating features of the endoscope (100); or for advancing, withdrawing, and rotating flexible tools deployed to a surgical site via the endoscope (100); and/or various other kinds of controls as will be apparent to those skilled in the art in view of the teachings herein.

FIGS. 9A and 9B each show an exemplary distal tip (300) that may be utilized as the distal tip (106) of the endoscope (100), in accordance with embodiments of the present invention. The distal tip (300) may be statically positioned at the distal end of the shaft (104); or may be positioned at a distal end of a flexible or deflectable shaft that extends from or may be advanced and withdrawn through a channel of the distal tip (106). The distal tip (300) includes an instrument channel (302), through which flexible instruments and tools may be deployed through once the distal tip (300) is positioned at a desired location. By way of example only, channel (302) may be sized to accommodate a dilation catheter, a shaving instrument, an ablation instrument, and or various other kinds of instruments as will be apparent to those skilled in the art in view of the teachings herein. The distal tip (300) also includes a wavefront imaging device (304) and a set of lights (306) (e.g., LED, fiber optic, infrared light sources, etc.). The distal tip (300) also includes a set of irrigation diverters (308). Each irrigation diverter (308) is positioned proximately to a corresponding irrigation channel (e.g., the irrigation channel (310) visible in FIGS. 10A and 10B, which each show the distal tip (300) with one or both irrigation diverters (308) removed). Irrigation diverters (308) are adapted to receive and direct water or other liquids from the irrigation channel (310) to wash the wavefront imaging device (304), the lights (306), or both.

The wavefront imaging device (304) may comprise a digital camera (e.g., one or more image sensors) or imaging device capable of capturing and transmitting image data to the processor (12); or another device of the IGS navigation system (10) capable of storing and processing the image data to generate 3D image data. While some conventional 3D image capture devices may require two or more offset imaging devices that are capable of actively and independently focusing on a target, the wavefront imaging device (304) of the present example is capable of producing 3D image data from a single camera or image sensor using wavefront sampling techniques. In order to produce image data compatible with wavefront sampling techniques, the wavefront imaging device (304) includes one or more apertures that are positioned between the target and the camera lens; and that are off-axis or offset from the optical axis of the lens. When a target is imaged with the wavefront imaging device (304), a single image will be produced that will contain multiple unfocused depictions of the target, offset from each other based upon the positions of the aperture(s). The distance between each unfocused image may be used to calculate the depth or distance to the imaged target. Images captured by the wavefront imaging device (304) may be provided as input to a wavefront sampling algorithm, such as Frigerio's multi image procedure, in order to produce a 3D depth map and 3D model of the imaged object.

FIG. 11 shows one example of the wavefront imaging device (304), which implements a static optical system (320), in accordance with an embodiment of the present invention. The static optical system (320) includes a lens (326) with a first static aperture (328a) and a second static aperture (328b) positioned between the lens (326) and a target (330). The apertures (328a, 328b) are diametrically opposed and offset from the optical axis of the lens (326). Two or more apertures may be used, with a larger number of apertures improving accuracy of the resulting 3D image, while requiring additional time for imaging of a target and processing of image data. A lower number of apertures may reduce the time required for imaging and processing, in exchange for a loss of accuracy of the resulting 3D image. Aperture size may be increased or decreased in order control the depth of field of captured images. Reducing the distance between the apertures and the lens (326) may also produce improved results for wavefront sampling.

During imaging, the lens (326) will receive a first unfocused image (332a) and a second unfocused image (332b) of the target (330) through the apertures (328a, 328b), and will direct the first unfocused image (332a) and the second unfocused image (332b) onto the image plane (322). The image plane (322) may be provided by a CCD, CMOS, or other image sensor. An image offset (336) between the resulting images (332a, 332b) may then be determined and used as part of a wavefront sampling technique to determine pixel depth and produce a 3D model of the target (330).

FIG. 12 shows another example of the wavefront imaging device (304), implemented as an active optical system (340), in accordance with an embodiment of the present invention. The active optical system (340) includes the lens (326) with a single aperture (344a) positioned on a rotatable aperture plate (342) between the lens (326) and the target (330). The aperture plate (342) may be electronically and automatically rotated during imaging in order to move the single aperture (344a) from its shown position, to a second position (344b), a third position (344c), and so on throughout the rotation. In this example, the aperture plate (342) rotates about a rotation axis that is coaxial with the optical axis of lens (326). As with the static optical system (320), the lens (326) receives unfocused images of the target (330) during rotation of the aperture plate (342). Thus, a first unfocused image (346a), a second unfocused image (346b), a third unfocused image (346c), and so on are projected onto the image plane (322) at offset positions following a rotation path (348). This image data captured by the image plane (322) may then be used with wavefront sampling techniques to determine pixel depth produced a 3D model of the target (330).

FIG. 13 depicts a set of exemplary steps (400) that may be performed to produce a three-dimensional image model using an imaging device such as the imaging device (304), in accordance with an embodiment of the present invention. Image data may be captured (block 402) as described above in the context of FIGS. 11 and 12 and processed into 3D image data by applying a wavefront sampling algorithm (e.g., Frigerio's multi image procedure or another similar algorithm). As an example, such a process may include defining (block 404) an anchor image to use as a basis for determining offsets of the other images. The anchor image may be an arbitrarily selected image, an image that is most centrally located relative to two or more other images; or may be selected based upon other criteria. An optical flow approach may then be used to calculate pixel displacement (block 406) between the anchor image and other images. A circle may be fit (block 408) to points across the images, and the rotational diameter (or other offset value) may be determined (block 410). The rotational diameter may then be used to calculate (block 412) pixel depth for a plurality of pixels of the image. Pixel depth may then be used to build (block 414) a 3D model of imaged object or target.

The distal tip (300) and wavefront imaging device (304) may be advantageous in that they provide a solution for 3D imaging of a surgical site that has a relatively low complexity (e.g., as compared to a 3D camera with multiple independently and actively oriented cameras); and that can be mounted on the end of an instrument such as at the distal tip (106), or that can be mounted on a flexible or deflectable shaft. Advantages in reduced complexity may be particularly realized when the wavefront imaging device (304) is implemented with the static optical system (320), which can be implemented with a small physical size requirement and minimal supporting requirements due to low power use and lack of moving components (e.g., such as the aperture plate (342) or independently orientable cameras).

As noted above, endoscope (100) of the present example includes a position sensor (110) that is operable to provide signals indicating the real time position of distal tip (106) in three-dimensional space. As imaging device (304) captures images, the image data from imaging device (304) may be stored in connection with the position data from position sensor (110), such that IGS navigation system (10) (and/or some other computer system) may correlate each captured image with its corresponding location in three-dimensional space. This will enable IGS navigation system (10) to correlate images captured with imaging device (304) with one or more preoperatively obtained images (e.g., a CT or MRI scan, 3-D map, etc.). This aspect of the invention along with the dual camera 3D imaging below can be used with the image correction aspect of the invention described above.

Endoscope with Dual Camera 3D Imaging

FIGS. 14A and 14B each show another exemplary distal tip (500) that may be utilized as the distal tip (106) of the endoscope (100), in accordance with other embodiments of the present invention. The distal tip (500) may be statically positioned at the distal end of the shaft (104); or may be positioned at a distal end of a flexible or deflectable shaft that extends from or may be advanced and withdrawn through a channel of the distal tip (106). The distal tip (500) includes an instrument channel (502), having similar features and function as the instrument channel (302); a light (506), having similar features and function as the light (306); and a set of irrigation channels (510), having similar features and function as the irrigation channels (310). The distal tip (500) also includes a first imaging device (504a) and a second imaging device (504b), which may comprise digital cameras (e.g., one or more image sensors) or other digital imaging devices capable of capturing image data at the distal tip (500) and transmitting it via a shaft or flexible shaft to the processor (12), coupling unit (42), or another device of the IGS navigation system (10) capable of processing captured images. With reference to FIG. 8B, it can be seen that the imaging devices (504a, 504b) are offset from each other along a first dimension (512), and at the same position along a second dimension (514).

FIGS. 15A and 15B show diagrammatic views of the distal tip (500) being used to image a target with passive stereo vision, a triangulation method that uses two or more imaging devices to obtain images from two or more different perspectives, in accordance with embodiments of the present invention. Images produced with passive stereo vision may be transformed into 3D image data algorithms such as a photogrammetric algorithm that determines pixel depth based on epipolar geometry. In FIG. 15A, it can be seen that the first imaging device (504a) and the second imaging device (504b) are arranged on the distal tip (500) such that they have parallel optical axes. When directed at a target (520), the first imaging device (504a) will capture a first field of view (522) of the target (520) while the second imaging device (504b) will capture a second field of view (526) of the target (520).

Since the two imaging devices (504a, 504b) have parallel optical axes (e.g., rather than independently focusing or orienting towards a converging point), the images captured by the devices may contain an overlapping portion of the target (520). For example, FIGS. 15A and 15B show the first field of view (522) and the second field of view (526), as well as a shared field of view (524), in which the target (520) will be captured by both imaging devices. With reference to FIG. 15B, it can be seen that the target (520) is substantially centered within the shared field of view (524). However, the target (520) is positioned on the right side of the first field of view (522), and on the left side of the second field of view (526). This disparity, or the distance that the target (520) is offset or displaced from the first field of view (522) to the second field of view (526), can be used to determine the distance between the imaging device and the target, and then the depth of pixels or portions of the captured image.

Determining and using disparity to determine depth is an example of passive triangulation. FIG. 16 depicts a set of exemplary steps (600) that may be performed to apply passive triangulation to image data, in accordance with an embodiment of the present invention. Image data may be captured (block 602) of a target by two or more statically arranged cameras, such as the first imaging device (504a) and the second imaging device (504b), resulting in two distinct images of the target from two different positions. A point (e.g., one or more pixels or portions of an image) may be picked (block 604) within one image, and the second image will be searched for a matching point (e.g., a portion of a target, such as the target (520), that are shared between the two images as illustrated in FIG. 9B). Performing image analysis of a point within a first image to find a matching point within an entirety of a second image may be both inefficient and inaccurate, resulting in a high processing requirement and an increased likelihood of false positive matching.

To improve the speed and accuracy of matching, the characteristics of an epipolar line associated with the two images may be determined (block 606). Epipolar geometry is a concept that may be applied to two images captured by cameras having a parallel optical axis in order to determine the disparity or distance between two matching pixels or points in an image without searching the entirety of an image for a match. FIGS. 17 and 19 depict diagrams illustrating the use of Epipolar geometry in stereo imaging, in accordance with embodiments of the present invention.

With reference to FIG. 17, which shows a diagram (700) that illustrates the relationship between disparity (e.g., the distance between two matching points in an image) and depth (e.g., the distance from the camera to the target, or a pixel or point in the target), a first camera (704) and a second camera (706) are arranged such that they have a parallel optical axis (e.g., lines F-B and G-D) through their respective lenses, which are arranged on the same lens plane (703). With this arrangement, a target A (702) is within the field of view of each camera. The distance between the optical axis of the cameras is BC+CD, and the triangles ACB and BFE have similar characteristics but are different in scale. Applying triangle geometry to FIG. 17, the displacement between two matching points or pixels in an image can be expressed as the distance between camera optical axes multiplied by the distance from the lens plane (703) to the image sensor, divided by the depth or distance to the target (702), or displacement=(BD*BF)/AC. This equation can be alternately used to determine or solve for the distance to the target (702), or AC, after determining the displacement or disparity.

To determine displacement between points or pixels in an image without searching the entire image, principles of Epipolar geometry illustrated FIG. 18 can be applied. Since the cameras (704, 706) have a fixed position relative to each other and parallel optical axes, an Epipolar line (712) can be determined that runs across a first image (708) and a second image (710), along which matching points or pixels can be found. As a result, when matching a point on the first image (708) to a point on the second image (710), only the portions of the second image (710) falling along the Epipolar line (712) need to be searched, rather than the entirety of the second image (710). By matching in this manner, the speed and accuracy at which points can be matched across images may be significantly increased.

After the points are matched (block 608), by applying Epipolar geometry or using another matching process, the displacement or disparity between matched points may be determined (block 610), which may then be used to determine (block 612) the depth or distance between the imaging device and the target. With the ability to determine (block 612) depth, a set of 3D image data and 3D model may be built (block 614).

As noted above, endoscope (100) of the present example includes a position sensor (110) that is operable to provide signals indicating the real time position of distal tip (106) in three-dimensional space. As imaging devices (504a, 504b) capture images, the image data from imaging devices (504a, 504b) may be stored in connection with the position data from position sensor (110), such that IGS navigation system (10) (and/or some other computer system) may correlate each captured image with its corresponding location in three-dimensional space. This will enable IGS navigation system (10) to correlate images captured with imaging devices (504a, 504b) with one or more preoperatively obtained images (e.g., a CT or MRI scan, 3-D map, etc.).

Method of Integrating 3D Imaging with Navigation

After producing 3D image data as described above, such image data can be used to provide additional features during IGS navigation. As an example, FIG. 19 depicts a flowchart of a set of steps (800) that may be performed to integrate a 3D model or 3D image data with IGS navigation, in accordance with an embodiment of the present invention. After capturing (block 802) image data using an appropriate imaging module (e.g., the waveform imaging device (304) of the distal tip (300), the set of cameras (504a, 504b) of the distal tip (500)) and building (block 804) a 3D model or other 3D image data set, such data may be used in various ways. For example, a composite image set may be created (block 806) by combining the 3D image data with other images, as well as with data associating image sets with each other using location data such as position and orientation. This may include, for example, associating a built (block 804) 3D model with a set of preoperatively captured CT images, a set of 2D images captured with a position tracked 2D endoscope during a procedure, or other similar information so that matching perspectives of a surgical site may be simultaneously displayed from multiple image sets.

As another example, a pre-operative comparison may be created (block 808) which compares a preoperatively captured CT scan or other 3D model with the built (block 804) 3D model. This may be useful to aid in planning or preparation for a surgical procedure, or to verify the accuracy and configuration of one or more 3D models. For example, a comparison of the built (block 804) 3D model to a set of CT images may help to identify missing or incorrect image or depth data in one or both models, to identify incorrectly associated location data in one or both models, or other errors that may be corrected by re-imaging to produce new 3D image data, or by reconfiguring or recalibrating to correct location data.

As another example, a post-operative comparison may be created (block 810) which compares post procedure CT scan, 3D models, or other image data with a built (block 804) 3D model to aid in assessing the success of a surgical procedure. A 3D model built (block 804) pre-operatively may be compared to a 3D model that is built (block 804) post operatively; or may be compared to post-operative CT scans or 2D imaging of a surgical site. Such comparison data may aid a clinician to assess the success or completeness of a surgical procedure, by physically comparing the anatomy from different perspectives available in 3D imaging.

By way of further example only, 3D image data captured or otherwise generated using distal tip (200) or distal tip (300) may be utilized in accordance with at least some of the teachings of U.S. Provisional Patent Application No. 62/782,608, entitled "3D Scanning of Nasal Tract with Deflectable Endoscope," filed Dec. 20, 2018, the disclosure of which is incorporated by reference herein; U.S. Pat. No. 8,199,988, entitled "Method and Apparatus for Combining 3D Dental Scans with Other 3D Data Sets," issued Jun. 12, 2012, the disclosure of which is incorporated by reference herein; and/or "U.S. Pat. No. 8,821,158, entitled "Method and Apparatus for Matching Digital Three-Dimensional Dental Models with Digital Three-Dimensional Cranio-Facial CAT Scan Records," issued Sep. 2, 2014, the disclosure of which is incorporated by reference herein.

EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A three-dimensional (3D) imaging system comprising: an endoscope comprising: a shaft having a distal tip, the shaft adapted to be inserted into a patient and positioned at a surgical site of the patient, a position sensor proximate to the distal tip and configured to produce a set of position signals based on the location of the endoscope during use, and an imaging module positioned at the distal tip and operable to capture a set of image data of the surgical site, wherein the set of image data comprises one or more two-dimensional (2D) images; and a processor communicatively coupled with the endoscope and configured to: receive the set of image data and the set of position signals from the endoscope, determine a set of perspective data based on the set of position signals, wherein the set of perspective data indicates the location of the endoscope during capture of the set of image data, perform an image depth analysis to determine a set of 3D characteristics of the set of image data, wherein the set of 3D characteristics comprises a depth of pixels in the one or more 2D images, create a set of 3D image data based on the one or more 2D images and the set of 3D characteristics, and associate the set of perspective data with the set of 3D image data.

Example 2

The 3D imaging system of example 1, wherein the imaging module comprises: a single lens, an aperture plate positioned between a first side of the single lens and the surgical site, the aperture plate comprising one or more apertures that are offset from the optical axis of the single lens, and an image pane positioned at a second side of the single lens to receive reflected light from the surgical site via the one or more apertures and the single lens, wherein the image pane is configured to produce the set of image data based on the reflected light.

Example 3

The 3D imaging system of example 2, wherein: the one or more apertures comprise at least two apertures positioned on the aperture plate and offset from the optical axis of the single lens, and the aperture plate has a fixed position and orientation relative to the lens.

Example 4

The 3D imaging system of any one or more of examples 2 through 3, wherein: the one or more apertures comprise a single aperture positioned on the aperture plate offset from the optical axis of the single lens, and the aperture plate is operable to rotate around its circular axis relative to the lens during image capture.

Example 5

The 3D imaging system of any one or more of examples 2 through 4, wherein the processor is configured to, when performing the image depth analysis: identify, within the set of image data, two or more unfocused images of the surgical site, determine a spatial relationship between the two or more unfocused images of the surgical site, and determine the depth of pixels of the set of image data based on the spatial relationship between the two or more unfocused images.

Example 6

The 3D imaging system of any one or more of examples 1 through 5, wherein the imaging module comprises two or more cameras, and wherein each of the two or more cameras is: statically positioned relative to every other camera of the two or more cameras, oriented to have a parallel optical axis with every other camera of the two or more cameras.

Example 7

The 3D imaging system of example 6, wherein the processor is further configured to, when performing the image depth analysis: identify a point in a first image of the set of image data, wherein the point comprises a portion of the surgical site that is present within both the first image captured by a first camera of the two or more cameras and within a second image captured by a second camera of the two or more cameras, identify the point in the second image, determine a displacement of the point from the first image to the second image, and determine the depth of pixels for the point based on the displacement.

Example 8

The 3D imaging system of example 7, wherein the processor is further configured to, when identifying the point in the second image: determine an Epipolar line for the first image and the second image based on the static position of the first camera relative to the second camera, and search for the point in the second image along the Epipolar line while excluding portions of the second image that do not fall along the Epipolar line.

Example 9

The 3D imaging system of any one or more of examples 1 through 8, wherein the processor is further configured to: associate the set of 3D image data and the set of perspective data with a coordinate system of an image guided surgery system, and display the set of 3D image data during an image guided surgery navigation procedure based upon the association with the coordinate system.

Example 10

The 3D imaging system of any one or more of examples 1 through 9, wherein: the position sensor is configured to produce the set of position signals based on the location and orientation of the endoscope during use, the set of perspective data indicates the location and orientation of the endoscope during capture of the set of image data, and the processor is further configured to provide the set of 3D image data and the set of perspective data to an image guided surgery navigation system.

Example 11

The 3D imaging system of any one or more of examples 1 through 10, wherein the processor is further configured to: receive an input from a user defining a perspective relative to the surgical site, determine a first portion of the set of 3D image data depicting the surgical site from the perspective based on identifying the perspective within the set of perspective data, and display the first portion of the set of 3D image data on a display.

Example 12

The 3D imaging system of example 11, wherein the processor is further configured to: receive an indirect 3D scan of the surgical site and a set of scan perspective data associated with the indirect 3D scan, determine a second portion of the indirect 3D scan depicting the surgical site from the perspective based on identifying the perspective within the set of scan perspective data, and display the first portion of the set of 3D image data and the second portion of the indirect 3D scan on the display simultaneously.

Example 13

The 3D imaging system of example 12, wherein: the indirect 3D scan of the surgical site comprises pre-operatively captured image data, and the set of 3D image data comprises post-operatively captured image data.

Example 14

The 3D imaging system of any one or more of examples 12 through 13, wherein: the indirect 3D scan of the surgical site comprises pre-operatively captured image data, the set of 3D image data comprises pre-operatively captured image data, and the processor is further configured to: receive a scan adjustment input from a user, and reconfigure the association between the indirect 3D scan of the surgical site and the set of scan perspective data based on the scan adjustment input.

Example 15

A method for three-dimensional (3D) imaging comprising: deploying a distal tip of an endoscope to a surgical site of a patient, the distal tip comprising: an imaging module operable to capture image data of the surgical site, wherein captured image data comprises one or more two-dimensional (2D) images, and a position sensor proximate to the distal tip and configured to produce position signals based on the location of the endoscope; receiving a set of image data from the imaging module and a set of position signals from the position sensor; determining a set of perspective data based on the set of position signals, wherein the set of perspective data indicates the location of the endoscope during capture of the set of image data; performing an image depth analysis to determine a set of 3D characteristics of the set of image data, wherein the set of 3D characteristics comprises a depth of pixels in the one or more 2D images of the set of image data; creating a set of 3D image data based on the one or more 2D images of the set of image data and the set of 3D characteristics; and associating the set of perspective data with the set of 3D image data.

Example 16

The method of example 15, further comprising: associating the set of 3D image data and the set of perspective data with a coordinate system of an image guided surgery system; and displaying the set of 3D image data during an image guided surgery navigation procedure based upon the association with the coordinate system.

Example 17

The method of any one or more of examples 15 through 16, further comprising: receiving an input from a user defining a perspective relative to the surgical site; determining a first portion of the set of 3D image data depicting the surgical site from the perspective based on identifying the perspective within the set of perspective data; and displaying the first portion of the set of 3D image data on a display.

Example 18

The method of example 17, further comprising: receiving an indirect 3D scan of the surgical site and a set of scan perspective data associated with the indirect 3D scan; determining a second portion of the indirect 3D scan depicting the surgical site from the perspective based on identifying the perspective within the set of scan perspective data; and displaying the first portion of the set of 3D image data and the second portion of the indirect 3D scan on the display simultaneously

Example 19

The method of example 18, further comprising: receiving a scan adjustment input from a user; and reconfiguring the association between the indirect 3D scan of the surgical site and the set of scan perspective data based on the scan adjustment input; wherein: the indirect 3D scan of the surgical site comprises pre-operatively captured image data, and the set of 3D image data comprises pre-operatively captured image data.

Example 20

An image guided surgery (IGS) navigation system comprising a processor, a memory, and a display, the processor configured to: receive a set of image data produced by a tracked endoscope, the set of image data comprising one or more two-dimensional (2D) images; receive a set of perspective data produced by the tracked endoscope, wherein the set of perspective data indicates a location of the tracked endoscope during capture of the set of image data; perform an image depth analysis to determine a set of 3D characteristics of the set of image data, wherein the set of 3D characteristics comprises a depth of pixels in the one or more 2D images; create a set of 3D image data based on the one or more 2D images and the set of 3D characteristics; associate the set of perspective data with the set of 3D image data; and cause the display to show the set of 3D image data from a selected perspective based on the set of perspective data including the selected perspective.

Example 21

A system, comprising: a medical probe configured to be inserted into a cavity of an organ of a patient; a position and direction sensor in the medical probe operating in a sensor coordinate system; a camera in a distal edge of the medical probe operating in a sensor coordinate system; and a processor configured to: receive, from an imaging system operating in an image coordinate system, a three-dimensional image of the cavity comprising open space and organ tissue; receive, from the medical probe, signals indicating positions and respective directions of the distal edge of the medical probe inside the cavity; receive, from the camera of the probe, respective visualized locations inside the cavity; register the image coordinate system with the sensor coordinate system so as to identify one or more voxels in the three-dimensional image at the visualized locations; and when the identified voxels have density values in the received three-dimensional image that do not correspond to the open space, to update the density values of the identified voxels to correspond to the open space.

Example 22

The system according to example 21, wherein the imaging system comprises a computed tomography scanner.

Example 23

The system according to example 21, wherein the position and direction sensor comprises a magnetic field sensor.

Example 24

The system according to any of examples 21-23, wherein the processor is configured to form a correspondence between the density values visual effects, wherein a given visual effect corresponds to a given density value indicating the open space.

Example 25

The system according to example 24, wherein the visual effects are selected from a group consisting of colors, shadings and patterns.

Example 26

The system according to example 24, wherein the processor is configured to present the three-dimensional image on a display using the visual effects.

Example 27

The system according to example 26, wherein the given visual effect comprises a first given visual effect, and wherein prior to updating the density values, the processor is configured to present the three-dimensional image by presenting, using a second given visual effect different from the first given visual effect, the one or more identified voxels.

Example 28

The system according to example 27, wherein upon updating the density values, the processor is configured to present the three-dimensional image by presenting, using the first given visual effect, the one or more identified voxels. 9.

Example 29

The system according to example 28, wherein the processor is configured to, using a multi-view triangulation model, extract from the visual signals a distance of a location from the camera.

Example 30

A method, comprising: receiving, from an imaging system operating in an image coordinate system, a three-dimensional image of a cavity of an organ of a patient comprising open space and organ tissue; receiving, from a medical probe having a position and direction sensor and a camera, wherein the probe operates in a sensor coordinate system and inserted into the cavity: signals indicating positions and respective directions of a distal edge of the medical probe inside the cavity; and respective visualized locations inside the cavity; registering the image coordinate system with the sensor coordinate system so as to identify one or more voxels in the three-dimensional image at the visualized locations; and when the identified voxels have density values in the received three-dimensional image that do not correspond to the open space, updating the density values of the identified voxels to correspond to the open space.

Example 31

A computer software product, operated in conjunction with a probe that is configured for insertion into a cavity of an organ of a patient and includes a position and direction sensor operating in a sensor coordinate system and a camera in a distal edge of the medical probe operating in a sensor coordinate system, and the product comprising a non-transitory computer-readable medium, in which program instructions are stored, which instructions, when read by a computer, cause the computer to: receive, from an imaging system operating in an image coordinate system, a three-dimensional image of the cavity comprising open space and organ tissue; receive, from the medical probe, signals indicating positions and respective directions of the distal edge of the medical probe inside the cavity; receive respective visualized locations the wall of the cavity; register the image coordinate system with the sensor coordinate system so as to identify one or more voxels in the three-dimensional image at the visualized locations; and when the identified voxels have density values in the received three-dimensional image that do not correspond to the open space, to update the density values of the identified voxels to correspond to the open space.

Miscellaneous

While embodiments herein describe a processor using magnetic P&D sensing and optical visualization by a camera, applied to correct an outdated CT image, using other types of position sensing, and visualization, to correct other types of medical images is considered to be within the spirit and scope of the present invention. For example, ultrasound visualization can be used with an ultrasound transducer instead of a camera. In addition, although the embodiments described herein mainly address ENT procedures, the methods and systems described herein can also be used in other applications, such as in other cavities of organs of the body.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. An apparatus, comprising:
   (a) a shaft extending along a longitudinal axis and having a distal tip, the distal tip having a radially outer periphery, the shaft adapted to be inserted into a patient and positioned at a surgical site of the patient;
   (b) a passive stereo vision device positioned at the distal tip and operable to capture a set of image data comprising one or more two-dimensional images, wherein the passive stereo vision device comprises two or more cameras arranged radially inwardly of the radially outer periphery of the distal tip of the shaft, wherein each camera of the two or more cameras are:
      (i) statically positioned relative to every other camera of the two or more cameras, and
      (ii) oriented to have a parallel optical axis with every other camera of the two or more cameras, wherein a first optical axis of a first camera of the two or more cameras is disposed on a first side of the longitudinal axis, wherein a second optical axis of a second camera of the two or more cameras is disposed on a second side of the longitudinal axis; and
   (c) a channel extending through the shaft and to the distal tip, the channel being configured to provide one or more of:
      (i) passage of a working instrument, or
      (ii) communication of a fluid.

2. The apparatus of claim 1, wherein the two or more cameras of the passive stereo vision device are offset from each other along a first dimension and are at a same position as each other along a second dimension.

3. The apparatus of claim 1, wherein the two or more cameras of the passive stereo vision device are configured to capture two or more fields of view of the surgical site, respectively, wherein the two or more fields of view overlap each other.

4. The apparatus of claim 1, wherein the two or more cameras of the passive stereo vision device have two or more lenses arranged on a same lens plane as each other.

5. The apparatus of claim 1, wherein the shaft is operable to provide deflection of the distal tip.

6. The apparatus of claim 1, wherein the distal tip includes at least one illuminating element configured to illuminate at least one field of view of the passive stereo vision device.

7. The apparatus of claim 1, further comprising at least one irrigation diverter configured to direct at least a portion of irrigation fluid from the channel to the passive stereo vision device.

8. The apparatus of claim 1, further comprising a position sensor proximate to the distal tip and configured to produce a set of position signals based on a location of the apparatus during use.

9. A three-dimensional imaging system comprising:
   (a) the apparatus of claim 1; and
   (b) a processor communicatively coupled with the apparatus and configured to perform an image depth analysis to determine a set of three-dimensional characteristics for each of the one or more two-dimensional images, wherein the image depth analysis comprises a passive stereo vision technique.

10. A three-dimensional imaging system comprising:
    (a) an endoscope comprising:
       (i) a shaft extending along a longitudinal axis and having a distal tip, the distal tip having a radially outer periphery, the shaft adapted to be inserted into a patient and positioned at a surgical site of the patient, and
       (ii) a passive stereo vision device positioned at the distal tip and operable to capture a set of image data comprising one or more two-dimensional images, wherein the passive stereo vision device comprises two or more cameras arranged radially inwardly of the radially outer periphery of the distal tip of the shaft, wherein each of the two or more cameras are:
          (A) statically positioned relative to every other camera of the two or more cameras, and
          (B) oriented to have a parallel optical axis with every other camera of the two or more cameras, wherein a first optical axis of a first camera of the two or more cameras is disposed on a first side of the longitudinal axis, wherein a second optical axis of a second camera of the two or more cameras is disposed on a second side of the longitudinal axis; and
    (b) a processor communicatively coupled with the endoscope and configured to:
       (i) receive the set of image data from the endoscope, and
       (ii) perform an image depth analysis to determine a set of 3D characteristics for each of the one or more two-dimensional images, wherein the set of three-dimensional characteristics comprises a depth of pixels, wherein the image depth analysis comprises a passive stereo vision technique comprising:
          (A) identifying a point in a first image of the set of image data, wherein the point comprises a portion of the surgical site that is present within both the first image captured by a first camera of the two or more cameras and within a second image captured by a second camera of the two or more cameras,
          (B) identifying the point in the second image,
          (C) determining a displacement of the point from the first image to the second image, and
          (D) determining the depth of pixels for the point based on the displacement.

11. The three-dimensional imaging system of claim 10, wherein the processor is further configured to, when identifying the point in the second image, determine an Epipolar line for the first image and the second image based on the static position of the first camera relative to the second camera.

12. The three-dimensional imaging system of claim 11, wherein the processor is further configured to, when identifying the point in the second image, search for the point in the second image along the Epipolar line while excluding portions of the second image that do not fall along the Epipolar line.

13. The three-dimensional imaging system of claim 10, wherein the processor is further configured to create a set of three-dimensional image data based on the one or more two-dimensional images and the set of three-dimensional characteristics.

14. The three-dimensional imaging system of claim 13, wherein the endoscope further comprises a position sensor proximate to the distal tip and configured to produce a set of position signals based on a location of the endoscope during use, wherein the processor is further configured to:
 (i) receive the set of position signals from the endoscope,
 (ii) determine a set of perspective data based on the set of position signals, wherein the set of perspective data indicates the location of the endoscope during capture of each of the one or more two-dimensional images,
 (iii) receive an input from a user defining a perspective relative to the surgical site,
 (iv) determine a first portion of the set of three-dimensional image data depicting the surgical site from the perspective based on identifying the perspective within the set of perspective data, and
 (v) display the first portion of the set of three-dimensional image data on a display.

15. The three-dimensional imaging system of claim 14, wherein the processor is further configured to:
 (i) receive an indirect three-dimensional scan of the surgical site and a set of scan perspective data associated with the indirect three-dimensional scan,
 (ii) determine a second portion of the indirect three-dimensional scan depicting the surgical site from the perspective based on identifying the perspective within the set of scan perspective data, and
 (iii) display the first portion of the set of three-dimensional image data and the second portion of the indirect three-dimensional scan on the display simultaneously.

16. The three-dimensional imaging system of claim 15, wherein the indirect three-dimensional scan of the surgical site comprises pre-operatively captured image data.

17. The three-dimensional imaging system of claim 16, wherein the set of three-dimensional image data comprises post-operatively captured image data.

18. The three-dimensional imaging system of claim 16, wherein the set of three-dimensional image data comprises pre-operatively captured image data.

19. The three-dimensional imaging system of claim 18, wherein the processor is further configured to:
 (i) receive a scan adjustment input from a user, and
 (ii) reconfigure the association between the indirect three-dimensional scan of the surgical site and the set of scan perspective data based on the scan adjustment input.

20. A method for three-dimensional imaging comprising:
 (a) deploying a distal tip of a shaft of an endoscope to a surgical site of a patient, the shaft extending along a longitudinal axis, the distal tip having a radially outer periphery and comprising a passive stereo vision device operable to capture image data comprising one or more two-dimensional images, wherein the passive stereo vision device comprises two or more cameras arranged radially inwardly of the radially outer periphery of the distal tip of the shaft, wherein each of the two or more cameras are statically positioned relative to every other camera of the two or more cameras and oriented to have a parallel optical axis with every other camera of the two or more cameras, wherein a first optical axis of a first camera of the two or more cameras is disposed on a first side of the longitudinal axis, wherein a second optical axis of a second camera of the two or more cameras is disposed on a second side of the longitudinal axis;
 (b) receiving a set of image data from the passive stereo vision device; and
 (c) performing an image depth analysis to determine a set of three-dimensional characteristics for each of the one or more two-dimensional images, wherein the set of three-dimensional characteristics comprises a depth of pixels, wherein the image depth analysis comprises a passive stereo vision technique comprising:
  (i) identifying a point in a first image of the set of image data, wherein the point comprises a portion of the surgical site that is present within both the first image captured by a first camera of the two or more cameras and within a second image captured by a second camera of the two or more cameras,
  (ii) identifying the point in the second image,
  (iii) determining a displacement of the point from the first image to the second image, and
  (iv) determining the depth of pixels for the point based on the displacement.

* * * * *